United States Patent
Van Dun et al.

(10) Patent No.: US 10,941,411 B2
(45) Date of Patent: Mar. 9, 2021

(54) MODIFIED GENE RESULTING IN PARTHENOCARPIC FRUIT SET

(71) Applicant: RIJK ZWAAN ZAADTEELT EN ZAADHANDEL B.V., De Lier (NL)

(72) Inventors: Cornelis Maria Petrus Van Dun, De Lier (NL); Magdalena Barbara Lastdrager, De Lier (NL); Lena Johanna Huijbregts-Doorduin, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 309 days.

(21) Appl. No.: 15/656,109

(22) Filed: Jul. 21, 2017

(65) Prior Publication Data

US 2017/0335339 A1   Nov. 23, 2017

Related U.S. Application Data

(63) Continuation-in-part of application No. PCT/EP2016/051900, filed on Jan. 29, 2016.

(30) Foreign Application Priority Data

Jan. 30, 2015 (NL) .................................... 2014215

(51) Int. Cl.
| | | |
|---|---|---|
| *C12N 15/82* | (2006.01) | |
| *A01H 5/08* | (2018.01) | |
| *C07K 14/415* | (2006.01) | |
| *C12N 9/90* | (2006.01) | |

(52) U.S. Cl.
CPC .......... *C12N 15/8261* (2013.01); *A01H 5/08* (2013.01); *C07K 14/415* (2013.01); *C12N 9/90* (2013.01); *C12N 15/8287* (2013.01); *C12N 15/8294* (2013.01); *C12Y 502/01008* (2013.01)

(58) Field of Classification Search
None
See application file for complete search history.

(56) References Cited

U.S. PATENT DOCUMENTS

| 9,253,953 B2 | 2/2016 | Eggink et al. |
| 2013/0239258 A1 | 9/2013 | Eggink et al. |
| 2016/0057960 A1 | 3/2016 | Eggink et al. |

FOREIGN PATENT DOCUMENTS

| EP | 2 568 047 | 3/2013 |
| WO | 2012/087140 | 6/2012 |

OTHER PUBLICATIONS

Lazar et al (1988, "Transforming Growth Factor Alpha: Mutation of Aspartic Acid 47 and Leucine 48 Results in Different Biological Activities", Molecular and Cellular Biology, 8:1247-1252).*
Hill et al (1998, "Functional Analysis of Conserved Histidine's in ADP-Glucose Pyrophosphorylase from *Escherichia coli*", Biochemical and Biophysical Research Communications, 244(2): 573-577).*
Bowie et al, (1990, "Deciphering the Message in Protein Sequences: Tolerance to Amino Acid Substitutions", Science 247:1306-1310).*
McConnell et al, (2001, "Role of Phabulosa and Phavoluta in Determining Radial Patterning in Shoots", Nature 411 (6838): 709-713).*
Pattison et al (2012, Genbank Accession No. HQ127078).*
Henikoff et al (Jun. 2004, "Tilling. Traditional Mutagenesis Meets Functional Genomics", Plant Physiology 135: 630-636).*
Mounet et al (2012, "Down-Regulation of a Single Auxin Efflux Transport Protein in Tomato Induces Precocious Fruit Development", Journal of Experimental Botany 63(13): 4901-4917).*
International Search Report and Written Opinion of the International Searching Authority dated Mar. 29, 2016 which issued during prosecution of International Application No. PCT/EP2016/051900.
Friml et al. "AtPIN4 mediates sink-driven auxin gradients and root patterning in Arabidopsis" Cell, Mar. 2002, 108(5):661-673.
Krecek et al. "The PIN-Formed (PIN) protein family of auxin transporters", Genome Biology, Jan. 2009, 10 (12):249.
Mounet et al. "Down-regulation of a single auxin efflux transport protein in tomato induces precocious fruit development" Journal of Experimental Botany, Aug. 2012, 63(13):4901-4917.
Uniprot. "Subname: Full=Uncharacterized protein {EC0:0000313| EMBL:KGN51517.1};" retrieved from EBI accession No. Uniprot:A0A0A0KT02, Jan. 7, 2015.
Uniprot. "RecName: Full=Auxin efflux carrier component {EC0:0000256|RuleBase: RU362108};" retrieved from EBI accession No. Uniprot:D7URM6, Oct. 5, 2010.

* cited by examiner

*Primary Examiner* — Stuart F Baum
(74) *Attorney, Agent, or Firm* — Duane Morris LLP; Thomas J. Kowalski; Deborah L. Lu

(57) ABSTRACT

The invention relates to a modified PIN4 gene, the wild type of which is as identified in SEQ ID No. 1, encoding the protein of SEQ ID No. 5, or the wild type of which encodes a protein that has a sequence similarity of at least 80% to SEQ ID No. 5, which modified PIN4 gene encodes a protein that comprises an amino acid change as a result of the modification, and which modified protein is capable of inducing parthenocarpic fruit set when present in a plant. The invention also relates to plants and fruits that carry the gene. Such plants are capable of parthenocarpic fruit set and the fruits do not contain seeds. The invention further relates to use of the gene in breeding and producing plants capable of parthenocarpic fruit set.

11 Claims, 14 Drawing Sheets
(3 of 14 Drawing Sheet(s) Filed in Color)
Specification includes a Sequence Listing.

Fig. 1A

SEQ ID No. 1
PIN4_g59516_Chrom Wild-type gDNA *Cucumis melo*

GTAAGTAACTGGAAAAGAAGACATCCATGTCAGTGAAAGGGGATTTGCACATGAAAACTGCCACTTGTGCAAACAAGGTC
CCACCATAACCCCAATTGGGTTAAACTAACCATAGTAGGCGGTTAACTTCCTTTTTACAAACCAAAAAAAGAACCTCACTTC
TTTCTTCTATATATACTCCACCAATCTCTCTCTCTCCTCTCCGCTCTCTTCTCTTTCTTTCCCTCTCTCTAAATTCATTCAATTTTT
TtTTtCTTTTTTTTtATAAAACTTCAAAAAAAaaTAAAAAAAAAaCCTATTTTTTTTTTtACGTCTTGTCGTCCCTTCCCTTTCTC
ATAGTTCCCATCACAAAGCTTTAGCAGTCGATTGCTGCAGAACGACATATATTCCCACCCTCTTCGTTTTAGTTAGTTAACTA
ACCGAAAATTTTATTtCCTTTTTtACCCTTCCTTTCTCATCTAATTTATCTTCCACTTGCCACTGACCAAaCAAAACCGCCATGA
TTTCATGGAAGGATCTTTACACCGTCTTAACGGCGGTTATCCCTCTTTACGTTGCCATGATTTTGGCTTACGGTTCTGTTCGG
TGGTGGAAGATTTTCACTCCCGATCAATGCTCTGGAATCAATCGTTTTGTTGCCATTTTCGCCGTTCCTCTTCTTTCCTTTCAT
TTTATATCTACTAATGATCCTTACGCTATGAACTTCCGTTTCATCGCTGCTGATACACTTCAGAAGATTATTATGTTGTTTTt
CTTGGGATTTGGACTAATTTCACTAAGAATGGGAGTCTGGAATGGATGATTACTATTTTCTCTCTCTCCACCCTTCCGAATA
CCCTGGTTATGGGGATTCCTCTGTTGATTGCCATGTACGGTGAGTACAGTGGGAGTCTGATGGTACAGGTGGTGGTTTTGC
AGTGTATTATTTGGTACACGCTTTTGCTTTTTCTGTTTGAATATCGTGGTGCGAAGATTCTCATTATGGAGCAATTTCCCGAG
ACGGCTGCTTCCATTGTTTCGTTTAAAGTTGATTCTGATGTGGTTTCATTAGATGGTAGAGATTTTCTTGAGACTGATGCTG
AGATTGGAGATGACGGAAAGCTTCACGTGACGGTGAGGAAATCCAATGCTTCTCGTCGCTCTCTTGGACCTTGTTCACTTC
CGGCATTAACGCCTAGACCTTCTAATCTCACTGGTGCGGAGATTTATAGCTTGAGTTCTTCTCGAAACCCTACTCCTCGTGG
CTCCAATTTCAACCATTCCGATTTCTATTCTATGATGGGATTTCAAGGTCGATTGTCTAACTTCGGACCTGGAGATTTGTATT
CCGTTCAATCCTCCAGAGGTCCGACTCCCCGGCCGTCCAATTTTGAAGAGAACTCTGCCGTTCAGCCTCAAACTGCGTCTCC
GAGGTTCGGGTTTTACCCGGCTCAAACTGTGCCCTCGTCTTACCCGGCTCCAAATCCCGAATTCACTAAAACCGCTAAAATC
CCTCAGCCACCGCCGCCTCCTCCGCCGCAGCAACCACAGCAACAACCGCAGAACGCTAAACCAAACCATGACGCGAAGGA
GCTTCACATGTTTGTTTGGAGCTCTAGCGCTTCACCAGTCTCTGAAGGCGCCGGTGGACTTCACATTTTCGCCGGGAATGA
AGTAGCCGGAGCCGAGCAATCTGGACGGTCCGATCAAGGCGCCAAGGAGATCCGGATGCTCGTGGCTGATCATCCACAA
AACGGGGAAAaCAAAGGTAACAAACAATCATAATAAAATAAAATAAATAGTCGTAATATATTTTGAACTTCCAATTAATCT
CCATAACTCAAATTTTCCAGAAAATGAGGGCTATGTAGGTGAAGCCTTTAGTTTCAGCGGCAAAGAAGGGGAAGATGAAA
GAGATGATCAGAAAGAAGGACCCACAGGCTCAACCGGAGATCAACTCCACGGGAAAGTTTCCGCCGGCGCACCGGACGG
CGTGAACTCAAAACTAATGCCGCCGGCAAGCGTGATGACCCGTTTGATTCTAATCATGGTTTGGCGGAAACTGATCAGAA
ATCCCAACACGTATTCAAGTCTGATCGGATTAATTTGGTCGCTCATTTCATTCCGGTAAGCCAAACCCATTTTGATTATTACA
CAGTAGATTGGATTGAAACATCCATATCAACTAACTATTGTTCCCTCTTATTTGGATTTGTGTCTATGAAATTGTGCTCCGTA
TTTATTGTTTGTTCATGGACTTGTCTTTCTTGTTGGGTCTGTGATGAAATTTTGCAGGTGGCATGTGGCCATGCCTAAAATA
ATAGAGAAATCGATCTCCATACTCTCTGATGCAGGACTTGGAATGGCTATGTTTAGCTTAGGTAAGTGGTCGTTATCTTTAT
TTATTATCTTTCTTTAATTAATTATTCTTAAAATTCTAATGAATTAAGAATTAAGACTTAAGGAAAGAAAAAAGAAATCACTT
GTTCTTTTGGTCTTTGTTTGAAACATATTATGATCATGTTGTCACGTAAGTATCCTAATAATTGAAGGGAAACTTAATGTAAT
CATTACAAAGACAGAAAAAAaTATATATCTTAAAGAGTTGATTTGTTTTTtAATCCGAGAATTAAGAAAAGGTTAGTGTATA
CCTTTATTATTTAGATAATTAAACAAATAAGTGTATTATTTGGTAGTGTGTATAGAGGCTGGCAAAGAATGGGTATTCTTTT
TTGTGTGCATTATTTTTTGGTCACATTGTATGTCTGAAAAGGGGATGGGAAGGCTTTTAATCTTGGGCCTTGACCAGCCGA
CATGAGGGCCCAGTGGGCCCAAATGGGGTAAAGGTCTGAACTGGGTGGTCCAAGGATGGGTGGGCCGGAGTTAATGCC
ATCCATTGTACAGTCCAAATTAGTGAAAGTAGTTGAAGTGTAAATTCATGTATTTCTTTTtCCATTTTtCTTTTtCATTGAAATT
CTTCGTTTGGAAAaTTGACTAGTGTTTGTTTATTGATGAAAAaTAAAaTAAAaTAAAGGTATATTTATGGGACTACAACCAA
AGATGATAGCATGTGGCAACTCTGTTGCTACTTTTGCCATGGCTATCAGATTCCTAACTGGGCCAGCCGTTATGGCTATTGC
TTCCATCGCTATTGGCTTACGCGGAACCCTCCTCCGCGTTGCTATTGTTCAGGTAAGTTCTTTTAATTACCTTGAGATGACTT
TTGAATATAGTTTTTTCTAAAATGATATATGACTGTAAATTTGCCTTCTGAGTCAATCGGTAATTTTAAAATAGTATTTATAG
TAAGTGATCTATGTTCAAAATTAGGTGGTCTTAAGATAACTAGAGCTATAATATTGTCAACAGTACTCTTATAATGAGTAAT
ACTTCTTAATGATATACTCTTATCTTTTAAACTTCAAAACTTGTATCTAAATTTTATTATGTATGATTTTTCTTTTACATTTTACT
ATATCTTTTAGTACTCTGACCCTAATAGAATTATATGAGGTTTTGGTATGTGAaaTAAACAGTGAAAAGCTGATGTATCATC
CCTGTGCTATTATTGTAGGCGGCATTGCCTCAAGGAATTGTACCATTCGTGTTTGCAAAAGAGTACAACGTCCATCCAGCTA

Fig. 1B (continued)

TTCTAAGCACTGGGTAACCAATACTCAACCTTTCAAAATGCCTTTTCTTTGCAGCTTTTtGGTCCTTTTTtCAGGCCCTCTTTTt
AATATAAAAGCTTCTCCTCATCCTTCTATGGCCATCATTATTGAGTTTGGTACACTTGCTATCATCATATTTTGCAGGGTTAT
CTTTGGAATGCTTATAGCTCTCCCCATTACTCTGCTCTACTATGTTCTGCTGGGTCTGTAAATTTCTCAAATTCCTTCCATATT
TCATAATGGTTTtGAGAAGAAGAAGACGAGGATGGCAATGACGACGGCGAAGAAGATCATAGGTTATATATAGAAGAAG
TTTGAGGAATGCTTAGAGAGAAGCCGCAGATGTTGGAAAAATGTCAAAGGTTTCATCAACTTTGCAAGAGATTTGATATG
AAAAGaGCTGTCTTTTGATCGTCTTCATATATAAAAGAaGAAAGAAAGAAAGAAAGAAAGAAAGAAAAAGATAGtCCGA
GCAaGAGGAAAAGAAAATCTTCGTTGCCATTTTGGGTGTAAATTtCTGACtGGAGTGGGAGaTCtATAGGGGAATTTAaaG
AtGTTTCTtGATtAGATTTTAaTtGAGgaGAAAAAAAAaCATCAATTATTCTTAATATTGTTTTTGTTTGGCAATAGATTTAGAA
ATtATTTTGTGTATGTCGtCTTCTTCTtcTTTTTTTTTttGGGTTTTGTAATTTGGTTATATATATTAGGTTG

SEQ ID No. 2
PIN4_g59516_CDS Wild-type *Cucumis melo*

ATGATTTCATGGAAGGATCTTTACACCGTCTTAACGGCGGTTATCCCTCTTTACGTTGCCATGATTTTGGCTTACGGTTCTGT
TCGGTGGTGGAAGATTTTCACTCCCGATCAATGCTCTGGAATCAATCGTTTTGTTGCCATTTTCGCCGTTCCTCTTCTTTCCTT
TCATTTTATATCTACTAATGATCCTTACGCTATGAACTTCCGTTTCATCGCTGCTGATACACTTCAGAAGATTATTATGTTGTT
TTTtCTTGGGATTTGGACTAATTTCACTAAGAATGGGAGTCTGGAATGGATGATTACTATTTTCTCTCTCTCCACCCTTCCGA
ATACCCTGGTTATGGGGATTCCTCTGTTGATTGCCATGTACGGTGAGTACAGTGGGAGTCTGATGGTACAGGTGGTGGTTT
TGCAGTGTATTATTTGGTACACGCTTTTGCTTTTTCTGTTTGAATATCGTGGTGCGAAGATTCTCATTATGGAGCAATTTCCC
GAGACGGCTGCTTCCATTGTTTCGTTTAAAGTTGATTCTGATGTGGTTTCATTAGATGGTAGAGATTTTCTTGAGACTGATG
CTGAGATTGGAGATGACGGAAAGCTTCACGTGACGGTGAGGAAATCCAATGCTTCTCGTCGCTCTCTTGGACCTTGTTCAC
TTCCGGCATTAACGCCTAGACCTTCTAATCTCACTGGTGCGGAGATTTATAGCTTGAGTTCTTCTCGAAACCCTACTCCTCGT
GGCTCCAATTTCAACCATTCCGATTTCTATTCTATGATGGGATTTCAAGGTCGATTGTCTAACTTCGGACCTGGAGATTTGT
ATTCCGTTCAATCCTCCAGAGGTCCGACTCCCCGGCCGTCCAATTTTGAAGAGAACTCTGCCGTTCAGCCTCAAACTGCGTC
TCCGAGGTTCGGGTTTTACCCGGCTCAAACTGTGCCCTCGTCTTACCCGGCTCCAAATCCCGAATTCACTAAAACCGCTAAA
ATCCCTCAGCCACCGCCGCCTCCTCCGCCGCAGCAACCACAGCAACAACCGCAGAACGCTAAACCAAACCATGACGCGAA
GGAGCTTCACATGTTTGTTTGGAGCTCTAGCGCTTCACCAGTCTCTGAAGGCGCCGGTGGACTTCACATTTTCGCCGGGAA
TGAAGTAGCCGGAGCCGAGCAATCTGGACGGTCCGATCAAGGCGCCAAGGAGATCCGGATGCTCGTGGCTGATCATCCA
CAAAACGGGGAAAaCAAAGAAAATGAGGGCTATGTAGGTGAAGCCTTTAGTTTCAGCGGCAAAGAAGGGGAAGATGAA
AGAGATGATCAGAAAGAAGGACCCACAGGCTCAACCGGAGATCAACTCCACGGGAAAGTTTCCGCCGGCGCACCGGACG
GCGTGAACTCAAAACTAATGCCGCCGGCAAGCGTGATGACCCGTTTGATTCTAATCATGGTTTGGCGGAAACTGATCAGA
AATCCCAACACGTATTCAAGTCTGATCGGATTAATTTGGTCGCTCATTTCATTCCGGTGGCATGTGGCCATGCCTAAAATAA
TAGAGAAATCGATCTCCATACTCTCTGATGCAGGACTTGGAATGGCTATGTTTAGCTTAGGTATATTTATGGGACTACAACC
AAAGATGATAGCATGTGGCAACTCTGTTGCTACTTTTGCCATGGCTATCAGATTCCTAACTGGGCCAGCCGTTATGGCTATT
GCTTCCATCGCTATTGGCTTACGCGGAACCCTCCTCCGCGTTGCTATTGTTCAGGCGGCATTGCCTCAAGGAATTGTACCAT
TCGTGTTTGCAAAAGAGTACAACGTCCATCCAGCTATTCTAAGCACTGGGGTTATCTTTGGAATGCTTATAGCTCTCCCCAT
TACTCTGCTCTACTATGTTCTGCTGGGTCTGTAA

Fig. 1C

SEQ ID No. 3
PIN4_g59516_CDS SNP C997>T997 (gDNA)=C497>T497(CDS)*Cucumis melo*

ATGATTTCATGGAAGGATCTTTACACCGTCTTAACGGCGGTTATCCCTCTTTACGTTGCCATGATTTTGGCTTACGGTTCTGT
TCGGTGGTGGAAGATTTTCACTCCCGATCAATGCTCTGGAATCAATCGTTTTGTTGCCATTTTCGCCGTTCCTCTTCTTTCCTT
TCATTTTATATCTACTAATGATCCTTACGCTATGAACTTCCGTTTCATCGCTGCTGATACACTTCAGAAGATTATTATGTTGTT
TTTtCTTGGGATTTGGACTAATTTCACTAAGAATGGGAGTCTGGAATGGATGATTACTATTTTCTCTCTCTCCACCCTTCCGA
ATACCCTGGTTATGGGGATTCCTCTGTTGATTGCCATGTACGGTGAGTACAGTGGGAGTCTGATGGTACAGGTGGTGGTTT
TGCAGTGTATTATTTGGTACACGCTTTTGCTTTTTCTGTTTGAATATCGTGGTGCGAAGATTCTCATTATGGAGCAATTTCTC
GAGACGGCTGCTTCCATTGTTTCGTTTAAAGTTGATTCTGATGTGGTTTCATTAGATGGTAGAGATTTTCTTGAGACTGATG
CTGAGATTGGAGATGACGGAAAGCTTCACGTGACGGTGAGGAAATCCAATGCTTCTCGTCGCTCTCTTGGACCTTGTTCAC
TTCCGGCATTAACGCCTAGACCTTCTAATCTCACTGGTGCGGAGATTTATAGCTTGAGTTCTTCTCGAAACCCTACTCCTCGT
GGCTCCAATTTCAACCATTCCGATTTCTATTCTATGATGGGATTTCAAGGTCGATTGTCTAACTTCGGACCTGGAGATTTGT
ATTCCGTTCAATCCTCCAGAGGTCCGACTCCCCGGCCGTCCAATTTTGAAGAGAACTCTGCCGTTCAGCCTCAAACTGCGTC
TCCGAGGTTCGGGTTTTACCCGGCTCAAACTGTGCCCTCGTCTTACCCGGCTCCAAATCCCGAATTCACTAAAACCGCTAAA
ATCCCTCAGCCACCGCCGCCTCCTCCGCCGCAGCAACCACAGCAACAACCGCAGAACGCTAAACCAAACCATGACGCGAA
GGAGCTTCACATGTTTGTTTGGAGCTCTAGCGCTTCACCAGTCTCTGAAGGCGCCGGTGGACTTCACATTTTCGCCGGGAA
TGAAGTAGCCGGAGCCGAGCAATCTGGACGGTCCGATCAAGGCGCCAAGGAGATCCGGATGCTCGTGGCTGATCATCCA
CAAAACGGGGAAAaCAAAGAAAATGAGGGCTATGTAGGTGAAGCCTTTAGTTTCAGCGGCAAAGAAGGGGAAGATGAA
AGAGATGATCAGAAAGAAGGACCCACAGGCTCAACCGGAGATCAACTCCACGGGAAAGTTTCCGCCGGCGCACCGGACG
GCGTGAACTCAAAACTAATGCCGCCGGCAAGCGTGATGACCCGTTTGATTCTAATCATGGTTTGGCGGAAACTGATCAGA
AATCCCAACACGTATTCAAGTCTGATCGGATTAATTTGGTCGCTCATTTCATTCCGGTGGCATGTGGCCATGCCTAAAATAA
TAGAGAAATCGATCTCCATACTCTCTGATGCAGGACTTGGAATGGCTATGTTTAGCTTAGGTATATTTATGGGACTACAACC
AAAGATGATAGCATGTGGCAACTCTGTTGCTACTTTTGCCATGGCTATCAGATTCCTAACTGGGCCAGCCGTTATGGCTATT
GCTTCCATCGCTATTGGCTTACGCGGAACCCTCCTCCGCGTTGCTATTGTTCAGGCGGCATTGCCTCAAGGAATTGTACCAT
TCGTGTTTGCAAAAGAGTACAACGTCCATCCAGCTATTCTAAGCACTGGGGTTATCTTTGGAATGCTTATAGCTCTCCCCAT
TACTCTGCTCTACTATGTTCTGCTGGGTCTGTAA

Fig. 1D

SEQ ID No. 4
PIN4_g59516_CDS SNP G1740>A1740 (gDNA)=G1240>A1240(CDS) *Cucumis melo*

ATGATTTCATGGAAGGATCTTTACACCGTCTTAACGGCGGTTATCCCTCTTTACGTTGCCATGATTTTGGCTTACGGTTCTGT
TCGGTGGTGGAAGATTTTCACTCCCGATCAATGCTCTGGAATCAATCGTTTTGTTGCCATTTTCGCCGTTCCTCTTCTTTCCTT
TCATTTTATATCTACTAATGATCCTTACGCTATGAACTTCCGTTTCATCGCTGCTGATACACTTCAGAAGATTATTATGTTGTT
TTTtCTTGGGATTTGGACTAATTTCACTAAGAATGGGAGTCTGGAATGGATGATTACTATTTTCTCTCTCTCCACCCTTCCGA
ATACCCTGGTTATGGGGATTCCTCTGTTGATTGCCATGTACGGTGAGTACAGTGGGAGTCTGATGGTACAGGTGGTGGTTT
TGCAGTGTATTATTTGGTACACGCTTTTGCTTTTTCTGTTTGAATATCGTGGTGCGAAGATTCTCATTATGGAGCAATTTCCC
GAGACGGCTGCTTCCATTGTTTCGTTTAAAGTTGATTCTGATGTGGTTTCATTAGATGGTAGAGATTTTCTTGAGACTGATG
CTGAGATTGGAGATGACGGAAAGCTTCACGTGACGGTGAGGAAATCCAATGCTTCTCGTCGCTCTCTTGGACCTTGTTCAC
TTCCGGCATTAACGCCTAGACCTTCTAATCTCACTGGTGCGGAGATTTATAGCTTGAGTTCTTCTCGAAACCCTACTCCTCGT
GGCTCCAATTTCAACCATTCCGATTTCTATTCTATGATGGGATTTCAAGGTCGATTGTCTAACTTCGGACCTGGAGATTTGT
ATTCCGTTCAATCCTCCAGAGGTCCGACTCCCCGGCCGTCCAATTTTGAAGAGAACTCTGCCGTTCAGCCTCAAACTGCGTC
TCCGAGGTTCGGGTTTTACCCGGCTCAAACTGTGCCCTCGTCTTACCCGGCTCCAAATCCCGAATTCACTAAAACCGCTAAA
ATCCCTCAGCCACCGCCGCCTCCTCCGCCGCAGCAACCACAGCAACAACCGCAGAACGCTAAACCAAACCATGACGCGAA
GGAGCTTCACATGTTTGTTTGGAGCTCTAGCGCTTCACCAGTCTCTGAAGGCGCCGGTGGACTTCACATTTTCGCCGGGAA
TGAAGTAGCCGGAGCCGAGCAATCTGGACGGTCCGATCAAGGCGCCAAGGAGATCCGGATGCTCGTGGCTGATCATCCA
CAAAACGGGAAAAaCAAAGAAAATGAGGGCTATGTAGGTGAAGCCTTTAGTTTCAGCGGCAAAGAAGGGGAAGATGAA
AGAGATGATCAGAAAGAAGGACCCACAGGCTCAACCGGAGATCAACTCCACGGGAAAGTTTCCGCCGGCGCACCGGACG
GCGTGAACTCAAAACTAATGCCGCCGGCAAGCGTGATGACCCGTTTGATTCTAATCATGGTTTGGCGGAAACTGATCAGA
AATCCCAACACGTATTCAAGTCTGATCGGATTAATTTGGTCGCTCATTTCATTCCGGTGGCATGTGGCCATGCCTAAAATAA
TAGAGAAATCGATCTCCATACTCTCTGATGCAGGACTTGGAATGGCTATGTTTAGCTTAGGTATATTTATGGGACTACAACC
AAAGATGATAGCATGTGGCAACTCTGTTGCTACTTTTGCCATGGCTATCAGATTCCTAACTGGGCCAGCCGTTATGGCTATT
GCTTCCATCGCTATTGGCTTACGCGGAACCCTCCTCCGCGTTGCTATTGTTCAGGCGGCATTGCCTCAAGGAATTGTACCAT
TCGTGTTTGCAAAAGAGTACAACGTCCATCCAGCTATTCTAAGCACTGGGGTTATCTTTGGAATGCTTATAGCTCTCCCCAT
TACTCTGCTCTACTATGTTCTGCTGGGTCTGTAA

Fig. 1E

SEQ ID No. 17
PIN4_g59516_CDS SNP C1384>A1384 (gDNA) = C884>A884 (CDS) *Cucumis melo*

```
ATGATTTCATGGAAGGATCTTTACACCGTCTTAACGGCGGTTATCCCTCTTTACGTTGCCATGATTTTGGCTTACGGTTCTGT
TCGGTGGTGGAAGATTTTCACTCCCGATCAATGCTCTGGAATCAATCGTTTTGTTGCCATTTTCGCCGTTCCTCTTCTTTCCTT
TCATTTTATATCTACTAATGATCCTTACGCTATGAACTTCCGTTTCATCGCTGCTGATACACTTCAGAAGATTATTATGTTGTT
TTTtCTTGGGATTTGGACTAATTTCACTAAGAATGGGAGTCTGGAATGGATGATTACTATTTTCTCTCTCTCCACCCTTCCGA
ATACCCTGGTTATGGGGATTCCTCTGTTGATTGCCATGTACGGTGAGTACAGTGGGAGTCTGATGGTACAGGTGGTGGTTT
TGCAGTGTATTATTTGGTACACGCTTTTGCTTTTTCTGTTTGAATATCGTGGTGCGAAGATTCTCATTATGGAGCAATTTCCC
GAGACGGCTGCTTCCATTGTTTCGTTTAAAGTTGATTCTGATGTGGTTTCATTAGATGGTAGAGATTTTCTTGAGACTGATG
CTGAGATTGGAGATGACGGAAAGCTTCACGTGACGGTGAGGAAATCCAATGCTTCTCGTCGCTCTCTTGGACCTTGTTCAC
TTCCGGCATTAACGCCTAGACCTTCTAATCTCACTGGTGCGGAGATTTATAGCTTGAGTTCTTCTCGAAACCCTACTCCTCGT
GGCTCCAATTTCAACCATTCCGATTTCTATTCTATGATGGGATTTCAAGGTCGATTGTCTAACTTCGGACCTGGAGATTTGT
ATTCCGTTCAATCCTCCAGAGGTCCGACTCCCCGGCCGTCCAATTTTGAAGAGAACTATGCCGTTCAGCCTCAAACTGCGTC
TCCGAGGTTCGGGTTTTACCCGGCTCAAACTGTGCCCTCGTCTTACCCGGCTCCAAATCCCGAATTCACTAAAACCGCTAAA
ATCCCTCAGCCACCGCCGCCTCCTCCGCCGCAGCAACCACAGCAACAACCGCAGAACGCTAAACCAAACCATGACGCGAA
GGAGCTTCACATGTTTGTTTGGAGCTCTAGCGCTTCACCAGTCTCTGAAGGCGCCGGTGGACTTCACATTTTCGCCGGGAA
TGAAGTAGCCGGAGCCGAGCAATCTGGACGGTCCGATCAAGGCGCCAAGGAGATCCGGATGCTCGTGGCTGATCATCCA
CAAAACGGGGAAAaCAAAGAAAATGAGGGCTATGTAGGTGAAGCCTTTAGTTTCAGCGGCAAAGAAGGGGAAGATGAA
AGAGATGATCAGAAAGAAGGACCCACAGGCTCAACCGGAGATCAACTCCACGGGAAAGTTTCCGCCGGCGCACCGGACG
GCGTGAACTCAAAACTAATGCCGCCGGCAAGCGTGATGACCCGTTTGATTCTAATCATGGTTTGGCGGAAACTGATCAGA
AATCCCAACACGTATTCAAGTCTGATCGGATTAATTTGGTCGCTCATTTCATTCCGGTGGCATGTGGCCATGCCTAAAATAA
TAGAGAAATCGATCTCCATACTCTCTGATGCAGGACTTGGAATGGCTATGTTAGCTTAGGTATATTTATGGGACTACAACC
AAAGATGATAGCATGTGGCAACTCTGTTGCTACTTTTGCCATGGCTATCAGATTCCTAACTGGGCCAGCCGTTATGGCTATT
GCTTCCATCGCTATTGGCTTACGCGGAACCCTCCTCCGCGTTGCTATTGTTCAGGCGGCATTGCCTCAAGGAATTGTACCAT
TCGTGTTTGCAAAAGAGTACAACGTCCATCCAGCTATTCTAAGCACTGGGGTTATCTTTGGAATGCTTATAGCTCTCCCCAT
TACTCTGCTCTACTATGTTCTGCTGGGTCTGTAA
```

Fig. 2A

SEQ ID No. 5
PIN4_g59516 protein Wild-type *Cucumis melo*

MISWKDLYTVLTAVIPLYVAMILAYGSVRWWKIFTPDQCSGINRFVAIFAVPLLSFHFISTNDPYAMNFRFIAADTLQKIIMLFFLG
IWTNFTKNGSLEWMITIFSLSTLPNTLVMGIPLLIAMYGEYSGSLMVQVVVLQCIIWYTLLLFLFEYRGAKILIMEQFPETAASIVSF
KVDSDVVSLDGRDFLETDAEIGDDGKLHVTVRKSNASRRSLGPCSLPALTPRPSNLTGAEIYSLSSSRNPTPRGSNFNHSDFYSM
MGFQGRLSNFGPGDLYSVQSSRGPTPRPSNFEENSAVQPQTASPRFGFYPAQTVPSSYPAPNPEFTKTAKIPQPPPPPPPQQP
QQQPQNAKPNHDAKELHMFVWSSSASPVSEGAGGLHIFAGNEVAGAEQSGRSDQGAKEIRMLVADHPQNGENKENEGYV
GEAFSFSGKEGEDERDDQKEGPTGSTGDQLHGKVSAGAPDGVNSKLMPPASVMTRLILIMVWRKLIRNPNTYSSLIGLIWSLISF
RWHVAMPKIIEKSISILSDAGLGMAMFSLGIFMGLQPKMIACGNSVATFAMAIRFLTGPAVMAIASIAIGLRGTLLRVAIVQAAL
PQGIVPFVFAKEYNVHPAILSTGVIFGMLIALPITLLYYVLLGL\*

SEQ ID No. 6
PIN4_g59516 protein P166L *Cucumis melo*

MISWKDLYTVLTAVIPLYVAMILAYGSVRWWKIFTPDQCSGINRFVAIFAVPLLSFHFISTNDPYAMNFRFIAADTLQKIIMLFFLG
IWTNFTKNGSLEWMITIFSLSTLPNTLVMGIPLLIAMYGEYSGSLMVQVVVLQCIIWYTLLLFLFEYRGAKILIMEQFLETAASIVSF
KVDSDVVSLDGRDFLETDAEIGDDGKLHVTVRKSNASRRSLGPCSLPALTPRPSNLTGAEIYSLSSSRNPTPRGSNFNHSDFYSM
MGFQGRLSNFGPGDLYSVQSSRGPTPRPSNFEENSAVQPQTASPRFGFYPAQTVPSSYPAPNPEFTKTAKIPQPPPPPPPQQP
QQQPQNAKPNHDAKELHMFVWSSSASPVSEGAGGLHIFAGNEVAGAEQSGRSDQGAKEIRMLVADHPQNGENKENEGYV
GEAFSFSGKEGEDERDDQKEGPTGSTGDQLHGKVSAGAPDGVNSKLMPPASVMTRLILIMVWRKLIRNPNTYSSLIGLIWSLISF
RWHVAMPKIIEKSISILSDAGLGMAMFSLGIFMGLQPKMIACGNSVATFAMAIRFLTGPAVMAIASIAIGLRGTLLRVAIVQAAL
PQGIVPFVFAKEYNVHPAILSTGVIFGMLIALPITLLYYVLLGL\*

SEQ ID No. 7
PIN4_g59516 protein E414K *Cucumis melo*

MISWKDLYTVLTAVIPLYVAMILAYGSVRWWKIFTPDQCSGINRFVAIFAVPLLSFHFISTNDPYAMNFRFIAADTLQKIIMLFFLG
IWTNFTKNGSLEWMITIFSLSTLPNTLVMGIPLLIAMYGEYSGSLMVQVVVLQCIIWYTLLLFLFEYRGAKILIMEQFPETAASIVSF
KVDSDVVSLDGRDFLETDAEIGDDGKLHVTVRKSNASRRSLGPCSLPALTPRPSNLTGAEIYSLSSSRNPTPRGSNFNHSDFYSM
MGFQGRLSNFGPGDLYSVQSSRGPTPRPSNFEENSAVQPQTASPRFGFYPAQTVPSSYPAPNPEFTKTAKIPQPPPPPPPQQP
QQQPQNAKPNHDAKELHMFVWSSSASPVSEGAGGLHIFAGNEVAGAEQSGRSDQGAKEIRMLVADHPQNGKNKENEGYV
GEAFSFSGKEGEDERDDQKEGPTGSTGDQLHGKVSAGAPDGVNSKLMPPASVMTRLILIMVWRKLIRNPNTYSSLIGLIWSLISF
RWHVAMPKIIEKSISILSDAGLGMAMFSLGIFMGLQPKMIACGNSVATFAMAIRFLTGPAVMAIASIAIGLRGTLLRVAIVQAAL
PQGIVPFVFAKEYNVHPAILSTGVIFGMLIALPITLLYYVLLGL\*

Fig. 2B

SEQ ID No. 18
PIN4_g59516 protein S295Y *Cucumis melo*

MISWKDLYTVLTAVIPLYVAMILAYGSVRWWKIFTPDQCSGINRFVAIFAVPLLSFHFISTNDPYAMNFRFIAADTLQKIIMLFFLG
IWTNFTKNGSLEWMITIFSLSTLPNTLVMGIPLLIAMYGEYSGSLMVQVVVLQCIIWYTLLLFLFEYRGAKILIMEQFPETAASIVSF
KVDSDVVSLDGRDFLETDAEIGDDGKLHVTVRKSNASRRSLGPCSLPALTPRPSNLTGAEIYSLSSSRNPTPRGSNFNHSDFYSM
MGFQGRLSNFGPGDLYSVQSSRGPTPRPSNFEEYAVQPQTASPRFGFYPAQTVPSSYPAPNPEFTKTAKIPQPPPPPPPQQP
QQQPQNAKPNHDAKELHMFVWSSSASPVSEGAGGLHIFAGNEVAGAEQSGRSDQGAKEIRMLVADHPQNGENKENEGYV
GEAFSFSGKEGEDERDDQKEGPTGSTGDQLHGKVSAGAPDGVNSKLMPPASVMTRLILIMVWRKLIRNPNTYSSLIGLIWSLISF
RWHVAMPKIIEKSISILSDAGLGMAMFSLGIFMGLQPKMIACGNSVATFAMAIRFLTGPAVMAIASIAIGLRGTLLRVAIVQAAL
PQGIVPFVFAKEYNVHPAILSTGVIFGMLIALPITLLYYVLLGL*

Fig. 3A

SEQ ID No. 12 - PIN4 protein sequence *Cucumis sativus*
MISWKDLYTVLTAVIPLYVAMILAYGSVRWWKIFTPDQCSGINRFVAIFAVPLLSFHFISSNDPYAMNFRFIAADTLQKIIMLFFLG
IWTNFTKNGSLEWMITIFSLSTLPNTLVMGIPLLIAMYGEYSGSLMVQVVVLQCIIWYTLLLFLFEYRGAKILIMEQFPETAASIVSF
KVDSDVVSLDGRDFLETDAEIGDDGKLHVTVRKSNASRRSLGPCSLPALTPRPSNLTGAEIYSLSSSRNPTPRGSNFNNSDFYSM
MGFQGRLSNFGPGDLYSVQSSRGPTPRPSNFEENSAVQPQTASPRFGFYPAQTVPSSYPAPNPEFTKTAKIPQPPPPPPPQQP
QQQPQNAKPNHDAKELHMFVWSSSASPVSEGAGGLHIFAGNEVAGAEQSGRSDQGAKEIRMLVADHPQNGENKENEGYV
GEAFSFSGKEGEDERDDQKEGPTGSTGDQLHGKVSAGAPDGVNSKLMPPASVMTRLILIMVWRKLIRNPNTYSSLIGLIWSLISF
RWHVAMPKIIEKSISILSDAGLGMAMFSLGIFMGLQPKMIACGNSVATFAMAIRFLTGPAVMAIASIAIGLRGTLLRVAIVQAAL
PQGIVPFVFAKEYNVHPAILSTGVIFGMLIALPITLLYYVLLGL

SEQ ID No. 13 – PIN4 protein sequence *Capsicum annuum*
MITWHDLYVVLTAVVPLYVAMILAYGSVRWWKIFSPDQCSGINRFVAIFAVPLLSFHFISLNNPYEMNFRFIAADSLQKVIMLVV
LALWANLTKNGSLEWSITIFSLSTLPNTLVMGIPLLIAMYGEYSGSLMVQVVVLQCIIWYTLLLFLFEYRGAKMLIMEQFPETAASI
VSFKVESDVVSLDGHDFLETDAEIGQDGKLHVTVRKSNASRRSFAMDDRPSNLTGAEIYSLSSSRNPTPRGSNFNHNDFYSMM
GFPGGRLSNFGPADMYSVQSSRGPTPRPSNFEENCAPGGLVQSSPRFGYFPAQQPAVPGSYPAPNPDIASTVPKSTKIQQPNV
QPQKQEGQHHHQQQQQPNAKANNHDAKELHMFVWSSSNSPVSEAGGLHVFGGNDFSANEQSGRSDGAKEIRMLVSDHP
QNGDTKGEFGGEDFTFGGANGGGKDGDEEKGDKEGPTGLTKLGSSSTSELHPKIGGGQDVGIGKQMPPASVMTRLILIMVW
RKLIRNPNTYSSLIGLTWSLVSFRWDVHMPKIIEKSISILSDAGLGMAMFSLGLFMALQPKIIACGNTVATFAMAVRFLTGPAVM
AAASIAVGLRGTLLHVAIVQAALPQGIVPFVFAKEYNVHPAILSTAVIFGMLIALPITLVYYIILGL

SEQ ID No. 14 – PIN4 protein sequence *Citrullus lanatus*
MISWKDLYTVLTAVIPLYVAMILAYGSVRWWKIFTPDQCSGINRFVAIFAVPLLSFHFISSNDPYAMNFRFIAADTLQKIIMLFFLG
IWTNFTKNGSLEWMITIFSLSTLPNTLVMGIPLLIAMYGEYSGSLMVQVVVLQCIIWYTLLLFLFEYRGAKILIMEQFPETAASIVSF
KVDSDVVSLDGRDFLETDAEIGDDGKLHVTVRKSNASRRSLGPCSLPALTPRPSNLTGAEIYSLSSSRNPTPRGSNFNHSDFYSM
MGFQGRLSNFGPGDLYSVQSSRGPTPRPSNFEENSAVQPQTASPRFGFYPAQTVPSSYPAPNPEFTKTTAKIPQPPPPPPPQQ
QPQPQPQNTKPNHDAKELHMFVWSSSASPVSEGGGGLHIFAGNELAGAEQSGRSDQGAKEIRMLVADHPQNGENKGVPES
EGYVGEAFSFSGKEGEEERDDQKEGPTGSTGDQLQGKVSAGAPDGGNSKLMPPASVMTRLILIMVWRKLIRNPNTYSSLIGLI
WSLISFRWHVAMPKIIEKSISILSDAGLGMAMFSLGIFMGLQPKMIACGNSVATFAMAIRFLTGPAVMAIASIAIGLRGTLLRVAI
VQAALPQGIVPFVFAKEYNVHPAILSTGVIFGMLIALPITLLYYVLLGL

SEQ ID No. 15 – PIN4 protein sequence *Solanum melongena*
MISWHDLYVVLTAVVPLYVAMILAYGSVRWWKIFSPDQCSGINRFVAIFAVPLLSFHFISLNNPYEMNFRFIAADSLQKVIMLVV
LALWANFTKNGSLEWSITIFSLSTLPNTLVMGIPLLIAMYGEYSGSLMVQVVVLQCIIWYTLLLFLFEYRGAKMLIMEQFPETAASI
VSFKVESDVVSLDGHDFLETDAEIGQDGKLHVTVRKSNASRRSFAMDHRPSNLTGAEIYSLSSSRNPTPRGSNFNHNDFYSMM
GFPGGRLSNFGPADMYSVQSSRGPTPRPSNFEENCAPGSLVQSSPRFGYFPAQQPAPGSYPAPNPEIASTVPKSTKPQQPNVQ
AQKQEVQQQQQPPNAKGINHDAKELHMFVWSSSNSPVSEAGGLHVFGGNDFSANEQSGRSDGAKEIRMLVSDHPQNGDT
KAIPQTGEFGGEDLTFRGANGGGKDGDEEKGEKEGPTGLTKLGSSSTSELHPKIAGGQDVDIGKQMPPASVMTRLILIMVWRK
LIRNPNTYSSLIGLVWSLIAFRWHVHMPKIIEKSISILSDAGLGMAMFSLGLFMALQPKIIACGNTVATFAMAVRFLTGPAVMAA
ASIAVGLRGTLLHVAIVQAALPQGIVPFVFAKEYNVHPAILSTAVIFGMLIALPITLVYYIILGL

Fig. 3B

SEQ ID No. 16 – PIN4 protein sequence *Solanum lycopersicum*
MITWHDLYVVLTAVVPLYVAMILAYGSVRWWKIFSPDQCSGINRFVAIFAVPLLSFHFIAMNNPYEMNFRFIAADSLQKVIMLV
VLSLWANLTKNGSLEWSITIFSLSTLPNTLVMGIPLLIAMYGEYSGSLMVQVVVLQCIIWYTLLLFLFEYRGAKMLIMEQFPETAAS
IVSFKVESDVVSLDGHDFLETDAEIGQDGKLHVTVRKSNASRRSFAMDHRPSNLTGAEIYSLSSSRNPTPRGSNFNHNDFYSMM
GFPGGRLSNFGPADMYSVQSSRGPTPRPSNFEENCAPGGLVQSSPRFGYFPTQQPAPGSYPAPNPEIASAGPKSTKPQQPNVQ
TQKQEVQQQQQQHQQPNAKANNHDAKELHMFVWSSSNSPVSEAGGLHVFGGNDFSANEQSGRSDGAKEIRMLVSDHTQ
NGDSKAIPQIGEFGGEDFTFGGANGGGKDGDEEKGEKEGPTGLTKLGSSSTSELHPKLAGVQDAGMGKQMPPASVMTRLILI
MVWRKLIRNPNTYSSLIGLIWSLISFRWHVHMPKIIEKSISILSDAGLGMAMFSLGLFMALQPKIIACGNTVATFAMAVRFLTGP
AVMAAASIAVGLRGTLLHVAIVQAALPQGIVPFVFAKEYNVHPAILSTAVIFGMLIALPITLVYYIILGL

Fig. 4A

PIN4.Orthologs.alignment
CLUSTAL O(1.2.1) multiple sequence alignment

```
SEQ ID No. 3     MISWKDLYTVLTAVIPLYVAMILAYGSVRWWKIFTPDQCSGINRFVAIFAVPLLSFHFIS
SEQ ID No. 12    MISWKDLYTVLTAVIPLYVAMILAYGSVRWWKIFTPDQCSGINRFVAIFAVPLLSFHFIS
SEQ ID No. 13    MISWKDLYTVLTAVIPLYVAMILAYGSVRWWKIFTPDQCSGINRFVAIFAVPLLSFHFIS
SEQ ID No. 14    MITWHDLYVVLTAVVPLYVAMILAYGSVRWWKIFSPDQCSGINRFVAIFAVPLLSFHFIS
SEQ ID No. 15    MISWHDLYVVLTAVVPLYVAMILAYGSVRWWKIFSPDQCSGINRFVAIFAVPLLSFHFIS
SEQ ID No. 16    MITWHDLYVVLTAVVPLYVAMILAYGSVRWWKIFSPDQCSGINRFVAIFAVPLLSFHFIA
                 **:*::***.*****:*****************:*.*.**************.****.

SEQ ID No. 3     TNDPYAMNFRFIAADTLQKIIMLFFLGIWTNFTKNGSLEWMITIFSLSTLPNTLVMGIPL
SEQ ID No. 12    SNDPYAMNFRFIAADTLQKIIMLFFLGIWTNFTKNGSLEWMITIFSLSTLPNTLVMGIPL
SEQ ID No. 13    SNDPYAMNFRFIAADTLQKIIMLFFLGIWTNFTKNGSLEWMITIFSLSTLPNTLVMGIPL
SEQ ID No. 14    LNNPYEMNFRFIAADSLQKVIMLVVLALWANLTKNGSLEWSITIFSLSTLPNTLVMGIPL
SEQ ID No. 15    LNNPYEMNFRFIAADSLQKVIMLVVLALWANLTKNGSLEWSITIFSLSTLPNTLVMGIPL
SEQ ID No. 16    MNNPYEMNFRFIAADSLQKVIMLVVLSLWANLTKNGSLEWSITIFSLSTLPNTLVMGIPL

SEQ ID No. 3     LIAMYGEYSGSLMVQVVVLQCIIWYTLLLFLFEYRGAKILIMEQFPETAASIVSFKVDSD
SEQ ID No. 12    LIAMYGEYSGSLMVQVVVLQCIIWYTLLLFLFEYRGAKILIMEQFPETAASIVSFKVDSD
SEQ ID No. 13    LIAMYGEYSGSLMVQVVVLQCIIWYTLLLFLFEYRGAKILIMEQFPETAASIVSFKVDSD
SEQ ID No. 14    LIAMYGEYSGSLMVQVVVLQCIIWYTLLLFLFEYRGAKMLIMEQFPETAASIVSFKVESD
SEQ ID No. 15    LIAMYGEYSGSLMVQVVVLQCIIWYTLLLFLFEYRGAKMLIMEQFPETAASIVSFKVESD
SEQ ID No. 16    LIAMYGEYSGSLMVQVVVLQCIIWYTLLLFLFEYRGAKMLIMEQFPETAASIVSFKVESD

SEQ ID No. 3     VVSLDGRDFLETDAEIGDDGKLHVTVRKSNASRRSLGPCSLPALTPRPSNLTGAEIYSLS
SEQ ID No. 12    VVSLDGRDFLETDAEIGDDGKLHVTVRKSNASRRSLGPCSLPALTPRPSNLTGAEIYSLS
SEQ ID No. 13    VVSLDGRDFLETDAEIGDDGKLHVTVRKSNASRRSLGPCSLPALTPRPSNLTGAEIYSLS
SEQ ID No. 14    VVSLDGHDFLETDAEIGQDGKLHVTVRKSNASRRSFA------MDDRPSNLTGAEIYSLS
SEQ ID No. 15    VVSLDGHDFLETDAEIGQDGKLHVTVRKSNASRRSFA------MDHRPSNLTGAEIYSLS
SEQ ID No. 16    VVSLDGHDFLETDAEIGQDGKLHVTVRKSNASRRSFA------MDHRPSNLTGAEIYSLS

SEQ ID No. 3     SSRNPTPRGSNFNHSDFYSMMGFQ-GRLSNFGPGDLYSVQSSRGPTPRPSNFEENSAVQP
SEQ ID No. 12    SSRNPTPRGSNFNNSDFYSMMGFQ-GRLSNFGPGDLYSVQSSRGPTPRPSNFEENSAVQP
SEQ ID No. 13    SSRNPTPRGSNFNHSDFYSMMGFQ-GRLSNFGPGDLYSVQSSRGPTPRPSNFEENSAVQP
SEQ ID No. 14    SSRNPTPRGSNFNHNDFYSMMGFPGGRLSNFGPADMYSVQSSRGPTPRPSNFEENCAPGG
SEQ ID No. 15    SSRNPTPRGSNFNHNDFYSMMGFPGGRLSNFGPADMYSVQSSRGPTPRPSNFEENCAPGS
SEQ ID No. 16    SSRNPTPRGSNFNHNDFYSMMGFPGGRLSNFGPADMYSVQSSRGPTPRPSNFEENCAPGG

SEQ ID No. 3     -QTASPRFGFYPAQT--VPSSYPAPNPEFTKT-AKIPQPPPPPP--------P-QQPQQQ
SEQ ID No. 12    -QTASPRFGFYPAQT--VPSSYPAPNPEFTKT-AKIPQPPPPPP--------P-QQPQQQ
SEQ ID No. 13    -QTASPRFGFYPAQT--VPSSYPAPNPEFTKTTAKIPQPPPPPP--------PQQQPQPQ
SEQ ID No. 14    LVQSSPRFGYFPAQQPAVPGSYPAPNPDIASTVPKSTKIQQPNVQPQKQEGQHHHQQQQQ
SEQ ID No. 15    LVQSSPRFGYFPAQQPA-PGSYPAPNPEIASTVPKSTKPQQPNVQAQKQEVQQQQ---QP
SEQ ID No. 16    LVQSSPRFGYFPTQQPA-PGSYPAPNPEIASAGPKSTKPQQPNVQTQKQEVQQQQQQHQQ

SEQ ID No. 3     PQNAKPNHDAKELHMFVWSSSASPVSEGAGGLHIFAGNEVAGAEQSGRSDQGAKEIRMLV
SEQ ID No. 12    PQNAKPNHDAKELHMFVWSSSASPVSEGAGGLHIFAGNEVAGAEQSGRSDQGAKEIRMLV
SEQ ID No. 13    PQNTKPNHDAKELHMFVWSSSASPVSEGGGGLHIFAGNELAGAEQSGRSDQGAKEIRMLV
SEQ ID No. 14    PNAKANNHDAKELHMFVWSSSNSPVSEA-GGLHVFGGNDFSANEQSGRSD-GAKEIRMLV
SEQ ID No. 15    PNAKGINHDAKELHMFVWSSSNSPVSEA-GGLHVFGGNDFSANEQSGRSD-GAKEIRMLV
SEQ ID No. 16    PNAKANNHDAKELHMFVWSSSNSPVSEA-GGLHVFGGNDFSANEQSGRSD-GAKEIRMLV
```

Fig. 4B

```
SEQ ID No. 5    ADHPQNGENK----ENEGYVGEAFSFSGKEGEDERD----DQKEGPTGSTG------DQLH
SEQ ID No. 12   ADHPQNGENK----ENEGYVGEAFSFSGKEGEDERD----DQKEGPTGSTG------DQLH
SEQ ID No. 13   ADHPQNGENKGVPESEGYVGEAFSFSGKEGEEERD----DQKEGPTGSTG------DQLQ
SEQ ID No. 14   SDHPQNGDTK------GEFGGEDFTFGGANGGGKDGDEEKGDKEGPTGLTKLGSSSTSELH
SEQ ID No. 15   SDHPQNGDTKAIPQTGEFGGEDLTFRGANGGGKDGDEEKGEKEGPTGLTKLGSSSTSELH
SEQ ID No. 16   SDHTQNGDSKAIPQIGEFGGEDFTFGGANGGGKDGDEEKGEKEGPTGLTKLGSSSTSELH
                 ** ***:.*      :  ** ::* *  :*   :      :******* *     .:*:

SEQ ID No. 5    GKVSAGAPDGVNSKLMPPASVMTRLIL IMVWRKLIRNPNTYSSLIGLIWSLISFRWHVAM
SEQ ID No. 12   GKVSAGAPDGVNSKLMPPASVMTRLIL IMVWRKLIRNPNTYSSLIGLIWSLISFRWHVAM
SEQ ID No. 13   GKVSAGAPDGGNSKLMPPASVMTRLIL IMVWRKLIRNPNTYSSLIGLIWSLISFRWHVAM
SEQ ID No. 14   PK-IGGGQDVGIGKQMPPASVMTRLIL IMVWRKLIRNPNTYSSLIGLTWSLVSFRWDVHM
SEQ ID No. 15   PK-IAGGQDVDIGKQMPPASVMTRLIL IMVWRKLIRNPNTYSSLIGLVWSLIAFRWHVHM
SEQ ID No. 16   PK-LAGVQDAGMGKQMPPASVMTRLIL IMVWRKLIRNPNTYSSLIGLIWSLISFRWHVHM
                 *   .*  *    *  ********************** ***:;***.* *

SEQ ID No. 5    PKIIEKSISILSDAGLGMAMFSLGIFMGLQPKMIACGNSVATFAMAIRFLTGPAVMAIAS
SEQ ID No. 12   PKIIEKSISILSDAGLGMAMFSLGIFMGLQPKMIACGNSVATFAMAIRFLTGPAVMAIAS
SEQ ID No. 13   PKIIEKSISILSDAGLGMAMFSLGIFMGLQPKMIACGNSVATFAMAIRFLTGPAVMAIAS
SEQ ID No. 14   PKIIEKSISILSDAGLGMAMFSLGLFMALQPKIIACGNTVATFAMAVRFLTGPAVMAAAS
SEQ ID No. 15   PKIIEKSISILSDAGLGMAMFSLGLFMALQPKIIACGNTVATFAMAVRFLTGPAVMAAAS
SEQ ID No. 16   PKIIEKSISILSDAGLGMAMFSLGLFMALQPKIIACGNTVATFAMAVRFLTGPAVMAAAS
                ************************:** ****:*****:******:*********** **

SEQ ID No. 5    IAIGLRGTLLRVAIVQAALPQGIVPFVFAKEYNVHPAILSTGVIFGMLIALPITLLYYVL
SEQ ID No. 12   IAIGLRGTLLRVAIVQAALPQGIVPFVFAKEYNVHPAILSTGVIFGMLIALPITLLYYVL
SEQ ID No. 13   IAIGLRGTLLRVAIVQAALPQGIVPFVFAKEYNVHPAILSTGVIFGMLIALPITLLYYVL
SEQ ID No. 14   IAVGLRGTLLHVAIVQAALPQGIVPFVFAKEYNVHPAILSTAVIFGMLIALPITLVYYII
SEQ ID No. 15   IAVGLRGTLLHVAIVQAALPQGIVPFVFAKEYNVHPAILSTAVIFGMLIALPITLVYYII
SEQ ID No. 16   IAVGLRGTLLHVAIVQAALPQGIVPFVFAKEYNVHPAILSTAVIFGMLIALPITLVYYII
                **;*******:*******************************.***********:**::

SEQ ID No. 5    LGL
SEQ ID No. 12   LGL
SEQ ID No. 13   LGL
SEQ ID No. 14   LGL
SEQ ID No. 15   LGL
SEQ ID No. 16   LGL
                ***
```

Fig. 6

SIAS
Secuences Identites And Similarities

IDENTITY RESULTS

| | melon | cucumber | watermelon | pepper | eggplant | tomato |
|---|---|---|---|---|---|---|
| melon | 100% | | | | | |
| cucumber | 99.69% | 100% | | | | |
| watermelon | 97.88% | 97.88% | 100% | | | |
| pepper | 76.62% | 76.47% | 76.01% | 100% | | |
| eggplant | 76.47% | 76.31% | 76.47% | 95.17% | 100% | |
| tomato | 76.31% | 76.16% | 76.47% | 95.17% | 95.77% | 100% |

SIMILARITY RESULTS

| | melon | cucumber | watermelon | pepper | eggplant | tomato |
|---|---|---|---|---|---|---|
| melon | 100% | | | | | |
| cucumber | 99.84% | 100% | | | | |
| watermelon | 98.49% | 98.34% | 100% | | | |
| pepper | 81.44% | 81.29% | 80.84% | 100% | | |
| eggplant | 81.14% | 80.99% | 81.44% | 95.92% | 100% | |
| tomato | 81.29% | 81.14% | 81.59% | 96.53% | 97.28% | 100% |

SEQUENCE LISTING

```
<160> NUMBER OF SEQ ID NOS: 18

<210> SEQ ID NO 1
<211> LENGTH: 4348
<212> TYPE: DNA
<213> ORGANISM: Cucumis melo

<400> SEQUENCE: 1
gtaagtaact ggaaaagaag acatccatgt cagtgaaagg ggatttgcac atgaaaactg      60
ccacttgtgc aaacaaggtc ccaccataac cccaattggg ttaaactaac catagtaggc     120
ggttaacttc cttttttacaa accaaaaaaa gaacctcact tctttcttct atatatactc     180
caccaatctc tctctctcct ctccgctctc ttctctttct ttccctctct ctaaattcat     240 tcaattttt ttttcttttt ttttataaaa cttcaaaaaa aaataaaaaa aaaacctatt     300
tttttttttt acgtcttgtc gtcccttccc tttctcatag ttcccatcac aaagctttag     360
cagtcgattg ctgcagaacg acatatattc ccaccctctt cgttttagtt agttaactaa     420
ccgaaaattt tatttccttt tttacccttc ctttctcatc taatttatct tccacttgcc     480
actgaccaaa caaaaccgcc atgatttcat ggaaggatct ttacaccgtc ttaacggcgg     540
ttatccctct ttacgttgcc atgatttttgg cttacggttc tgttcggtgg tggaagattt     600
tcactcccga tcaatgctct ggaatcaatc gttttgttgc cattttcgcc gttcctcttc     660
tttcctttca ttttatatct actaatgatc cttacgctat gaacttccgt ttcatcgctg     720
ctgatacact tcagaagatt attatgttgt tttttcttgg gatttggact aatttcacta     780
agaatgggag tctggaatgg atgattacta ttttctctct ctccaccctt ccgaataccc     840
```

```
tggttatggg gattcctctg ttgattgcca tgtacggtga gtacagtggg agtctgatgg     900
tacaggtggt ggttttgcag tgtattattt ggtacacgct tttgcttttt ctgtttgaat     960
atcgtggtgc gaagattctc attatggagc aatttcccga gacggctgct tccattgttt    1020
cgtttaaagt tgattctgat gtggtttcat tagatggtag agattttctt gagactgatg    1080
ctgagattgg agatgacgga aagcttcacg tgacggtgag gaaatccaat gcttctcgtc    1140
gctctcttgg accttgttca cttccggcat taacgcctag accttctaat ctcactggtg    1200
cggagattta tagcttgagt tcttctcgaa accctactcc tcgtggctcc aatttcaacc    1260
attccgattt ctattctatg atgggatttc aaggtcgatt gtctaacttc ggacctggag    1320
atttgtattc cgttcaatcc tccagaggtc cgactcccg gccgtccaat tttgaagaga     1380
actctgccgt tcagcctcaa actgcgtctc cgaggttcgg ttttacccg gctcaaactg     1440
tgccctcgtc ttacccggct ccaaatcccg aattcactaa aaccgctaaa atccctcagc    1500
caccgccgcc tcctccgccg cagcaaccac agcaacaacc gcagaacgct aaaccaaacc    1560
atgacgcgaa ggagcttcac atgtttgttt ggagctctag cgcttcacca gtctctgaag    1620
gcgccggtgg acttcacatt ttcgccggga atgaagtagc cggagccgag caatctggac    1680
ggtccgatca aggcgccaag gagatccgga tgctcgtggc tgatcatcca caaaacgggg    1740
aaaacaaagg taacaaacaa tcataataaa ataaaataaa tagtcgtaat atattttgaa    1800
cttccaatta atctccataa ctcaaatttt ccagaaaatg agggctatgt aggtgaagcc    1860
tttagtttca gcggcaaaga aggggaagat gaaagagatg atcagaaaga aggacccaca    1920
ggctcaaccg gagatcaact ccacgggaaa gtttccgccg gcgcaccgga cggcgtgaac    1980
tcaaaactaa tgccgccggc aagcgtgatg acccgtttga ttctaatcat ggtttggcgg    2040
aaactgatca gaaatcccaa cacgtattca agtctgatcg gattaatttg gtcgctcatt    2100
tcattccggt aagccaaacc cattttgatt attacacagt agattggatt gaaacatcca    2160
tatcaactaa ctattgttcc ctcttatttg gatttgtgtc tatgaaattg tgctccgtat    2220
ttattgtttg ttcatggact tgtctttctt gttgggtctg tgatgaaatt ttgcaggtgg    2280
catgtggcca tgcctaaaat aatagagaaa tcgatctcca tactctctga tgcaggactt    2340
ggaatggcta tgtttagctt aggtaagtgg tcgttatctt tatttattat ctttctttaa    2400
ttaattattc ttaaaattct aatgaattaa gaattaagac ttaaggaaag aaaaaagaaa    2460
tcacttgttc ttttggtctt tgtttgaaac atattatgat catgttgtca cgtaagtatc    2520
ctaataattg aagggaaact taatgtaatc attacaaaga cagaaaaaaa tatatatctt    2580
aaagagttga tttgtttttt aatccgagaa ttaagaaaag gttagtgtat acctttatta    2640
tttagataat taaacaaata agtgtattat ttggtagtgt gtatagaggc tggcaaagaa    2700
tgggtattct tttttgtgtg cattattttt tggtcacatt gtatgtctga aaaggggatg    2760
ggaaggcttt taatcttggg ccttgaccag ccgacatgag ggcccagtgg gcccaaatgg    2820
ggtaaaggtc tgaactgggt ggtccaagga tgggtgggcc ggagttaatg ccatccattg    2880
tacagtccaa attagtgaaa gtagttgaag tgtaaattca tgtatttctt tttccatttt    2940
tcttttcat tgaaattctt cgtttggaaa attgactagt gtttgtttat tgatgaaaaa      3000
taaaataaaa taaggtata tttatgggac tacaaccaaa gatgatagca tgtggcaact     3060
ctgttgctac ttttgccatg gctatcagat tcctaactgg gccagccgtt atggctattg    3120
cttccatcgc tattggctta cgcggaaccc tcctccgcgt tgctattgtt caggtaagtt    3180
ctttttaatta ccttgagatg acttttgaat atagtttttt ctaaaatgat atatgactgt   3240
```

```
aaatttgcct tctgagtcaa tcggtaattt taaaatagta tttatagtaa gtgatctatg    3300
ttcaaaatta ggtggtctta agataactag agctataata ttgtcaacag tactcttata    3360
atgagtaata cttcttaatg atatactctt atcttttaaa cttcaaaact tgtatctaaa    3420
ttttattatg tatgattttt cttttacatt ttactatatc ttttagtact ctgaccctaa    3480
tagaattata tgaggttttg gtatgtgaaa taaacagtga aaagctgatg tatcatccct    3540
gtgctattat tgtaggcggc attgcctcaa ggaattgtac cattcgtgtt tgcaaaagag    3600
tacaacgtcc atccagctat tctaagcact gggtaaccaa tactcaacct ttcaaaatgc    3660
cttttctttg cagcttttg gtccttttt caggccctct ttttaatata aaagcttctc      3720
ctcatccttc tatggccatc attattgagt ttggtacact tgctatcatc atattttgca    3780
gggttatctt tggaatgctt atagctctcc ccattactct gctctactat gttctgctgg    3840
gtctgtaaat ttctcaaatt ccttccatat ttcataatgg ttttgagaag aagaagacga    3900
ggatggcaat gacgacggcg aagaagatca taggttatat atagaagaag tttgaggaat    3960
gcttagagag aagccgcaga tgttggaaaa atgtcaaagg tttcatcaac tttgcaagag    4020
atttgatatg aaaagagctg tcttttgatc gtcttcatat ataaaagaaa gaaagaaaga    4080
aagaaagaaa gaaagaaaaa gatagtccga gcaagaggaa aagaaaatct tcgttgccat    4140
tttgggtgta aatttctgac tggagtggga gatctatagg ggaatttaaa gatgtttctt    4200
gattagattt taattgagga gaaaaaaaaa catcaattat tcttaatatt gttttgttt    4260 ggcaatagat ttagaaatta ttttgtgtat gtcgtcttct tcttcttttt tttttgggtt    4320
ttgtaatttg gttatatata ttaggttg                                      4348

<210> SEQ ID NO 2
<211> LENGTH: 1911
<212> TYPE: DNA
<213> ORGANISM: Cucumis melo

<400> SEQUENCE: 2
atgatttcat ggaaggatct ttacaccgtc ttaacggcgg ttatccctct ttacgttgcc      60
atgattttgg cttacggttc tgttcggtgg tggaagattt tcactcccga tcaatgctct    120
ggaatcaatc gttttgttgc catttttcgcc gttcctcttc tttcctttca ttttatatct    180
actaatgatc cttacgctat gaacttccgt ttcatcgctg ctgatacact tcagaagatt    240
attatgttgt tttttcttgg gatttggact aatttcacta agaatgggag tctggaatgg    300
atgattacta ttttctctct ctccacccct ccgaataccc tggttatggg gattcctctg    360
ttgattgcca tgtacggtga gtacagtggg agtctgatgg tacaggtggt ggttttgcag    420
tgtattattt ggtacacgct tttgcttttt ctgtttgaat atcgtggtgc gaagattctc    480
attatggagc aatttcccga gacggctgct tccattgttt cgtttaaagt tgattctgat    540
gtggtttcat tagatggtag agattttctt gagactgatg ctgagattgg agatgacgga    600
aagcttcacg tgacggtgag gaaatccaat gcttctcgtc gctctcttgg accttgttca    660
cttccggcat taacgcctag accttctaat ctcactggtg cggagattta tagcttgagt    720
tcttctcgaa accctactcc tcgtggctcc aatttcaacc attccgattt ctattctatg    780
atgggatttc aaggtcgatt gtctaacttc ggacctggag atttgtattc cgttcaatcc    840
tccagaggtc cgactcccg gccgtccaat tttgagagaa actctgccgt tcagcctcaa    900
actgcgtctc cgaggttcgg gttttacccg gctcaaactg tgccctcgtc ttacccggct    960
```

```
ccaaatcccg aattcactaa aaccgctaaa atccctcagc caccgccgcc tcctccgccg   1020
cagcaaccac agcaacaacc gcagaacgct aaaccaaacc atgacgcgaa ggagcttcac   1080
atgtttgttt ggagctctag cgcttcacca gtctctgaag gcgccggtgg acttcacatt   1140
ttcgccggga atgaagtagc cggagccgag caatctggac ggtccgatca aggcgccaag   1200
gagatccgga tgctcgtggc tgatcatcca caaaacgggg aaaacaaaga aaatgagggc   1260
tatgtaggtg aagcctttag tttcagcggc aaagaagggg aagatgaaag agatgatcag   1320
aaagaaggac ccacaggctc aaccggagat caactccacg ggaaagtttc cgccggcgca   1380
ccggacggcg tgaactcaaa actaatgccg ccggcaagcg tgatgacccg tttgattcta   1440
atcatggttt ggcggaaact gatcagaaat cccaacacgt attcaagtct gatcggatta   1500
atttggtcgc tcatttcatt ccggtggcat gtggccatgc ctaaaataat agagaaatcg   1560
atctccatac tctctgatgc aggacttgga atggctatgt ttagcttagg tatatttatg   1620
ggactacaac caaagatgat agcatgtggc aactctgttg ctacttttgc catggctatc   1680
agattcctaa ctgggccagc cgttatggct attgcttcca tcgctattgg cttacgcgga   1740
accctcctcc gcgttgctat tgttcaggcg gcattgcctc aaggaattgt accattcgtg   1800
tttgcaaaag agtacaacgt ccatccagct attctaagca ctggggttat ctttggaatg   1860
cttatagctc tccccattac tctgctctac tatgttctgc tgggtctgta a           1911

<210> SEQ ID NO 3
<211> LENGTH: 1911
<212> TYPE: DNA
<213> ORGANISM: Cucumis melo

<400> SEQUENCE: 3
atgatttcat ggaaggatct ttacaccgtc ttaacggcgg ttatccctct ttacgttgcc     60 atgatttttgg cttacggttc tgttcggtgg tggaagattt tcactcccga tcaatgctct   120
ggaatcaatc gttttgttgc cattttcgcc gttcctcttc tttccttttca ttttatatct   180 actaatgatc cttacgctat gaacttccgt ttcatcgctg ctgatacact tcagaagatt   240
attatgttgt tttttcttgg gatttggact aatttcacta agaatgggag tctggaatgg   300
atgattacta ttttctctct ctccacccct ccgaataccc tggttatggg gattcctctg   360
ttgattgcca tgtacggtga gtacagtggg agtctgatgg tacaggtggt ggttttgcag   420
tgtattattt ggtacacgct tttgcttttt ctgtttgaat atcgtggtgc gaagattctc   480
attatggagc aatttctcga cacgctgct tccattgttt cgtttaaagt tgattctgat   540
gtggtttcat tagatggtag agattttctt gagactgatg ctgagattgg agatgacgga   600
aagcttcacg tgacggtgag gaaatccaat gcttctcgtc gctctcttgg accttgttca   660
cttccggcat taacgcctag accttctaat ctcactggtg cggagattta tagcttgagt   720
tcttctcgaa accctactcc tcgtggctcc aatttcaacc attccgattt ctattctatg   780
atgggatttc aaggtcgatt gtctaacttc ggacctggag atttgtattc cgttcaatcc   840
tccagaggtc cgactccccg gccgtccaat tttgaagaga actctgccgt tcagcctcaa   900
actgcgtctc cgaggttcgg gttttacccg gctcaaactg tgccctcgtc ttacccggct   960
ccaaatcccg aattcactaa aaccgctaaa atccctcagc caccgccgcc tcctccgccg  1020
cagcaaccac agcaacaacc gcagaacgct aaaccaaacc atgacgcgaa ggagcttcac  1080
atgtttgttt ggagctctag cgcttcacca gtctctgaag gcgccggtgg acttcacatt  1140
ttcgccggga atgaagtagc cggagccgag caatctggac ggtccgatca aggcgccaag  1200
```

```
gagatccgga tgctcgtggc tgatcatcca caaaacgggg aaaacaaaga aaatgagggc   1260
tatgtaggtg aagcctttag tttcagcggc aaagaagggg aagatgaaag agatgatcag   1320
aaagaaggac ccacaggctc aaccggagat caactccacg ggaaagtttc cgccggcgca   1380
ccggacggcg tgaactcaaa actaatgccg ccggcaagcg tgatgacccg tttgattcta   1440
atcatggttt ggcggaaact gatcagaaat cccaacacgt attcaagtct gatcggatta   1500
atttggtcgc tcatttcatt ccggtggcat gtggccatgc ctaaaataat agagaaatcg   1560
atctccatac tctctgatgc aggacttgga atggctatgt ttagcttagg tatatttatg   1620
ggactacaac caaagatgat agcatgtggc aactctgttg ctacttttgc catggctatc   1680
agattcctaa ctgggccagc cgttatggct attgcttcca tcgctattgg cttacgcgga   1740
accctcctcc gcgttgctat tgttcaggcg gcattgcctc aaggaattgt accattcgtg   1800
tttgcaaaag agtacaacgt ccatccagct attctaagca ctggggttat ctttggaatg   1860
cttatagctc tccccattac tctgctctac tatgttctgc tgggtctgta a            1911

<210> SEQ ID NO 4
<211> LENGTH: 1911
<212> TYPE: DNA
<213> ORGANISM: Cucumis melo

<400> SEQUENCE: 4
atgatttcat ggaaggatct ttacaccgtc ttaacggcgg ttatccctct ttacgttgcc     60
atgattttgg cttacggttc tgttcggtgg tggaagattt tcactcccga tcaatgctct    120
ggaatcaatc gttttgttgc catttttcgcc gttcctcttc tttcctttca ttttatatct    180
actaatgatc cttacgctat gaacttccgt ttcatcgctg ctgatacact tcagaagatt    240
attatgttgt tttttcttgg gatttggact aatttcacta agaatgggag tctggaatgg    300
atgattacta ttttctctct ctccacccctt ccgaataccc tggttatggg gattcctctg    360
ttgattgcca tgtacggtga gtacagtggg agtctgatgg tacaggtggt ggttttgcag    420
tgtattattt ggtacacgct tttgcttttt ctgtttgaat atcgtggtgc gaagattctc    480
attatggagc aatttcccga cggctgct tccattgttt cgtttaaagt tgattctgat    540
gtggtttcat tagatggtag agattttctt gagactgatg ctgagattgg agatgacgga    600
aagcttcacg tgacggtgag gaaatccaat gcttctcgtc gctctcttgg accttgttca    660
cttccggcat taacgcctag accttctaat ctcactggtg cggagattta gcttgagt     720 tcttctcgaa accctactcc tcgtggctcc aatttcaacc attccgattt ctattctatg    780
atgggatttc aaggtcgatt gtctaacttc ggacctggag atttgtattc cgttcaatcc    840
tccagaggtc cgactccccg gccgtccaat tttgaagaga actctgccgt tcagcctcaa    900
actgcgtctc cgaggttcgg gttttacccg gctcaaactg tgccctcgtc ttacccggct    960
ccaaatcccg aattcactaa aaccgctaaa atccctcagc caccgccgcc tcctccgccg   1020
cagcaaccac agcaacaacc gcagaacgct aaaccaaacc atgacgcgaa ggagcttcac   1080
atgtttgttt ggagctctag cgcttcacca gtctctgaag gcgccggtgg acttcacatt   1140
ttcgccggga atgaagtagc cggagccgag caatctggac ggtccgatca aggcgccaag   1200
gagatccgga tgctcgtggc tgatcatcca caaaacggga aaacaaaga aatgagggc    1260 tatgtaggtg aagcctttag tttcagcggc aaagaagggg aagatgaaag agatgatcag   1320
aaagaaggac ccacaggctc aaccggagat caactccacg ggaaagtttc cgccggcgca   1380
```

```
ccggacggcg tgaactcaaa actaatgccg ccggcaagcg tgatgacccg tttgattcta    1440
atcatggttt ggcggaaact gatcagaaat cccaacacgt attcaagtct gatcggatta    1500
atttggtcgc tcatttcatt ccggtggcat gtggccatgc ctaaaataat agagaaatcg    1560
atctccatac tctctgatgc aggacttgga atggctatgt ttagcttagg tatatttatg    1620
ggactacaac caaagatgat agcatgtggc aactctgttg ctacttttgc catggctatc    1680
agattcctaa ctgggccagc cgttatggct attgcttcca tcgctattgg cttacgcgga    1740
accctcctcc gcgttgctat tgttcaggcg gcattgcctc aaggaattgt accattcgtg    1800
tttgcaaaag agtacaacgt ccatccagct attctaagca ctggggttat ctttggaatg    1860
cttatagctc tccccattac tctgctctac tatgttctgc tgggtctgta a            1911
```

<210> SEQ ID NO 5
<211> LENGTH: 636
<212> TYPE: PRT
<213> ORGANISM: Cucumis melo

<400> SEQUENCE: 5

```
Met Ile Ser Trp Lys Asp Leu Tyr Thr Val Leu Thr Ala Val Ile Pro
1               5                   10                  15

Leu Tyr Val Ala Met Ile Leu Ala Tyr Gly Ser Val Arg Trp Trp Lys
            20                  25                  30

Ile Phe Thr Pro Asp Gln Cys Ser Gly Ile Asn Arg Phe Val Ala Ile
        35                  40                  45

Phe Ala Val Pro Leu Leu Ser Phe His Phe Ile Ser Thr Asn Asp Pro
    50                  55                  60

Tyr Ala Met Asn Phe Arg Phe Ile Ala Ala Asp Thr Leu Gln Lys Ile
65                  70                  75                  80

Ile Met Leu Phe Phe Leu Gly Ile Trp Thr Asn Phe Thr Lys Asn Gly
                85                  90                  95

Ser Leu Glu Trp Met Ile Thr Ile Phe Ser Leu Ser Thr Leu Pro Asn
            100                 105                 110

Thr Leu Val Met Gly Ile Pro Leu Leu Ile Ala Met Tyr Gly Glu Tyr
        115                 120                 125

Ser Gly Ser Leu Met Val Gln Val Val Leu Gln Cys Ile Ile Trp
    130                 135                 140

Tyr Thr Leu Leu Leu Phe Leu Phe Glu Tyr Arg Gly Ala Lys Ile Leu
145                 150                 155                 160

Ile Met Glu Gln Phe Pro Glu Thr Ala Ala Ser Ile Val Ser Phe Lys
                165                 170                 175

Val Asp Ser Asp Val Val Ser Leu Asp Gly Arg Asp Phe Leu Glu Thr
            180                 185                 190

Asp Ala Glu Ile Gly Asp Asp Gly Lys Leu His Val Thr Val Arg Lys
        195                 200                 205

Ser Asn Ala Ser Arg Arg Ser Leu Gly Pro Cys Ser Leu Pro Ala Leu
    210                 215                 220

Thr Pro Arg Pro Ser Asn Leu Thr Gly Ala Glu Ile Tyr Ser Leu Ser
225                 230                 235                 240

Ser Ser Arg Asn Pro Thr Pro Arg Gly Ser Asn Phe Asn His Ser Asp
                245                 250                 255

Phe Tyr Ser Met Met Gly Phe Gln Gly Arg Leu Ser Asn Phe Gly Pro
            260                 265                 270

Gly Asp Leu Tyr Ser Val Gln Ser Ser Arg Gly Pro Thr Pro Arg Pro
        275                 280                 285
```

```
Ser Asn Phe Glu Glu Asn Ser Ala Val Gln Pro Gln Thr Ala Ser Pro
        290                 295                 300

Arg Phe Gly Phe Tyr Pro Ala Gln Thr Val Pro Ser Ser Tyr Pro Ala
305                 310                 315                 320

Pro Asn Pro Glu Phe Thr Lys Thr Ala Lys Ile Pro Gln Pro Pro Pro
                325                 330                 335

Pro Pro Pro Pro Gln Gln Pro Gln Gln Gln Pro Gln Asn Ala Lys Pro
            340                 345                 350

Asn His Asp Ala Lys Glu Leu His Met Phe Val Trp Ser Ser Ser Ala
            355                 360                 365

Ser Pro Val Ser Glu Gly Ala Gly Gly Leu His Ile Phe Ala Gly Asn
        370                 375                 380

Glu Val Ala Gly Ala Glu Gln Ser Gly Arg Ser Asp Gln Gly Ala Lys
385                 390                 395                 400

Glu Ile Arg Met Leu Val Ala Asp His Pro Gln Asn Gly Glu Asn Lys
                405                 410                 415

Glu Asn Glu Gly Tyr Val Gly Glu Ala Phe Ser Phe Ser Gly Lys Glu
            420                 425                 430

Gly Glu Asp Glu Arg Asp Asp Gln Lys Glu Gly Pro Thr Gly Ser Thr
        435                 440                 445

Gly Asp Gln Leu His Gly Lys Val Ser Ala Gly Ala Pro Asp Gly Val
450                 455                 460

Asn Ser Lys Leu Met Pro Pro Ala Ser Val Met Thr Arg Leu Ile Leu
465                 470                 475                 480

Ile Met Val Trp Arg Lys Leu Ile Arg Asn Pro Asn Thr Tyr Ser Ser
                485                 490                 495

Leu Ile Gly Leu Ile Trp Ser Leu Ile Ser Phe Arg Trp His Val Ala
            500                 505                 510

Met Pro Lys Ile Ile Glu Lys Ser Ile Ser Leu Ser Asp Ala Gly
        515                 520                 525

Leu Gly Met Ala Met Phe Ser Leu Gly Ile Phe Met Gly Leu Gln Pro
        530                 535                 540

Lys Met Ile Ala Cys Gly Asn Ser Val Ala Thr Phe Ala Met Ala Ile
545                 550                 555                 560

Arg Phe Leu Thr Gly Pro Ala Val Met Ala Ile Ala Ser Ile Ala Ile
                565                 570                 575

Gly Leu Arg Gly Thr Leu Leu Arg Val Ala Ile Val Gln Ala Ala Leu
            580                 585                 590

Pro Gln Gly Ile Val Pro Phe Val Phe Ala Lys Glu Tyr Asn Val His
        595                 600                 605

Pro Ala Ile Leu Ser Thr Gly Val Ile Phe Gly Met Leu Ile Ala Leu
610                 615                 620

Pro Ile Thr Leu Leu Tyr Tyr Val Leu Leu Gly Leu
625                 630                 635

<210> SEQ ID NO 6
<211> LENGTH: 636
<212> TYPE: PRT
<213> ORGANISM: Cucumis melo

<400> SEQUENCE: 6

Met Ile Ser Trp Lys Asp Leu Tyr Thr Val Leu Thr Ala Val Ile Pro
1               5                   10                  15

Leu Tyr Val Ala Met Ile Leu Ala Tyr Gly Ser Val Arg Trp Trp Lys
```

```
            20                  25                  30
Ile Phe Thr Pro Asp Gln Cys Ser Gly Ile Asn Arg Phe Val Ala Ile
            35                  40                  45

Phe Ala Val Pro Leu Leu Ser Phe His Phe Ile Ser Thr Asn Asp Pro
50                  55                  60

Tyr Ala Met Asn Phe Arg Phe Ile Ala Ala Asp Thr Leu Gln Lys Ile
65                  70                  75                  80

Ile Met Leu Phe Phe Leu Gly Ile Trp Thr Asn Phe Thr Lys Asn Gly
                85                  90                  95

Ser Leu Glu Trp Met Ile Thr Ile Phe Ser Leu Ser Thr Leu Pro Asn
            100                 105                 110

Thr Leu Val Met Gly Ile Pro Leu Leu Ile Ala Met Tyr Gly Glu Tyr
            115                 120                 125

Ser Gly Ser Leu Met Val Gln Val Val Leu Gln Cys Ile Ile Trp
            130                 135                 140

Tyr Thr Leu Leu Leu Phe Leu Phe Glu Tyr Arg Gly Ala Lys Ile Leu
145                 150                 155                 160

Ile Met Glu Gln Phe Leu Glu Thr Ala Ala Ser Ile Val Ser Phe Lys
                165                 170                 175

Val Asp Ser Asp Val Val Ser Leu Asp Gly Arg Asp Phe Leu Glu Thr
            180                 185                 190

Asp Ala Glu Ile Gly Asp Asp Gly Lys Leu His Val Thr Val Arg Lys
            195                 200                 205

Ser Asn Ala Ser Arg Arg Ser Leu Gly Pro Cys Ser Leu Pro Ala Leu
            210                 215                 220

Thr Pro Arg Pro Ser Asn Leu Thr Gly Ala Glu Ile Tyr Ser Leu Ser
225                 230                 235                 240

Ser Ser Arg Asn Pro Thr Pro Arg Gly Ser Asn Phe Asn His Ser Asp
                245                 250                 255

Phe Tyr Ser Met Met Gly Phe Gln Gly Arg Leu Ser Asn Phe Gly Pro
            260                 265                 270

Gly Asp Leu Tyr Ser Val Gln Ser Ser Arg Gly Pro Thr Pro Arg Pro
            275                 280                 285

Ser Asn Phe Glu Glu Asn Ser Ala Val Gln Pro Gln Thr Ala Ser Pro
290                 295                 300

Arg Phe Gly Phe Tyr Pro Ala Gln Thr Val Pro Ser Ser Tyr Pro Ala
305                 310                 315                 320

Pro Asn Pro Glu Phe Thr Lys Thr Ala Lys Ile Pro Gln Pro Pro
                325                 330                 335

Pro Pro Pro Pro Gln Gln Pro Gln Gln Gln Pro Gln Asn Ala Lys Pro
            340                 345                 350

Asn His Asp Ala Lys Glu Leu His Met Phe Val Trp Ser Ser Ser Ala
            355                 360                 365

Ser Pro Val Ser Glu Gly Ala Gly Gly Leu His Ile Phe Ala Gly Asn
            370                 375                 380

Glu Val Ala Gly Ala Glu Gln Ser Gly Arg Ser Asp Gln Gly Ala Lys
385                 390                 395                 400

Glu Ile Arg Met Leu Val Ala Asp His Pro Gln Asn Gly Glu Asn Lys
                405                 410                 415

Glu Asn Glu Gly Tyr Val Gly Glu Ala Phe Ser Phe Ser Gly Lys Glu
            420                 425                 430

Gly Glu Asp Glu Arg Asp Asp Gln Lys Glu Gly Pro Thr Gly Ser Thr
            435                 440                 445
```

-continued

```
Gly Asp Gln Leu His Gly Lys Val Ser Ala Gly Ala Pro Asp Gly Val
    450                 455                 460

Asn Ser Lys Leu Met Pro Ala Ser Val Met Thr Arg Leu Ile Leu
465                 470                 475                 480

Ile Met Val Trp Arg Lys Leu Ile Arg Asn Pro Asn Thr Tyr Ser Ser
                485                 490                 495

Leu Ile Gly Leu Ile Trp Ser Leu Ile Ser Phe Arg Trp His Val Ala
                500                 505                 510

Met Pro Lys Ile Ile Glu Lys Ser Ile Ser Leu Ser Asp Ala Gly
            515                 520                 525

Leu Gly Met Ala Met Phe Ser Leu Gly Ile Phe Met Gly Leu Gln Pro
    530                 535                 540

Lys Met Ile Ala Cys Gly Asn Ser Val Ala Thr Phe Ala Met Ala Ile
545                 550                 555                 560

Arg Phe Leu Thr Gly Pro Ala Val Met Ala Ile Ala Ser Ile Ala Ile
                565                 570                 575

Gly Leu Arg Gly Thr Leu Leu Arg Val Ala Ile Val Gln Ala Ala Leu
            580                 585                 590

Pro Gln Gly Ile Val Pro Phe Val Phe Ala Lys Glu Tyr Asn Val His
        595                 600                 605

Pro Ala Ile Leu Ser Thr Gly Val Ile Phe Gly Met Leu Ile Ala Leu
    610                 615                 620

Pro Ile Thr Leu Leu Tyr Tyr Val Leu Leu Gly Leu
625                 630                 635

<210> SEQ ID NO 7
<211> LENGTH: 636
<212> TYPE: PRT
<213> ORGANISM: Cucumis melo

<400> SEQUENCE: 7

Met Ile Ser Trp Lys Asp Leu Tyr Thr Val Leu Thr Ala Val Ile Pro
1               5                   10                  15

Leu Tyr Val Ala Met Ile Leu Ala Tyr Gly Ser Val Arg Trp Trp Lys
            20                  25                  30

Ile Phe Thr Pro Asp Gln Cys Ser Gly Ile Asn Arg Phe Val Ala Ile
        35                  40                  45

Phe Ala Val Pro Leu Leu Ser Phe His Phe Ile Ser Thr Asn Asp Pro
    50                  55                  60

Tyr Ala Met Asn Phe Arg Phe Ile Ala Ala Asp Thr Leu Gln Lys Ile
65              70                  75                  80

Ile Met Leu Phe Phe Leu Gly Ile Trp Thr Asn Phe Thr Lys Asn Gly
            85                  90                  95

Ser Leu Glu Trp Met Ile Thr Ile Phe Ser Leu Ser Thr Leu Pro Asn
        100                 105                 110

Thr Leu Val Met Gly Ile Pro Leu Leu Ile Ala Met Tyr Gly Glu Tyr
    115                 120                 125

Ser Gly Ser Leu Met Val Gln Val Val Leu Gln Cys Ile Ile Trp
130                 135                 140

Tyr Thr Leu Leu Leu Phe Leu Phe Glu Tyr Arg Gly Ala Lys Ile Leu
145                 150                 155                 160

Ile Met Glu Gln Phe Pro Glu Thr Ala Ala Ser Ile Val Ser Phe Lys
            165                 170                 175

Val Asp Ser Asp Val Val Ser Leu Asp Gly Arg Asp Phe Leu Glu Thr
```

```
            180                 185                 190
Asp Ala Glu Ile Gly Asp Asp Gly Lys Leu His Val Thr Val Arg Lys
            195                 200                 205
Ser Asn Ala Ser Arg Arg Ser Leu Gly Pro Cys Ser Leu Pro Ala Leu
            210                 215                 220
Thr Pro Arg Pro Ser Asn Leu Thr Gly Ala Glu Ile Tyr Ser Leu Ser
225                 230                 235                 240
Ser Ser Arg Asn Pro Thr Pro Arg Gly Ser Asn Phe Asn His Ser Asp
            245                 250                 255
Phe Tyr Ser Met Met Gly Phe Gln Gly Arg Leu Ser Asn Phe Gly Pro
            260                 265                 270
Gly Asp Leu Tyr Ser Val Gln Ser Ser Arg Gly Pro Thr Pro Arg Pro
            275                 280                 285
Ser Asn Phe Glu Glu Asn Ser Ala Val Gln Pro Gln Thr Ala Ser Pro
            290                 295                 300
Arg Phe Gly Phe Tyr Pro Ala Gln Thr Val Pro Ser Ser Tyr Pro Ala
305                 310                 315                 320
Pro Asn Pro Glu Phe Thr Lys Thr Ala Lys Ile Pro Gln Pro Pro Pro
            325                 330                 335
Pro Pro Pro Pro Gln Gln Pro Gln Gln Gln Pro Gln Asn Ala Lys Pro
            340                 345                 350
Asn His Asp Ala Lys Glu Leu His Met Phe Val Trp Ser Ser Ser Ala
            355                 360                 365
Ser Pro Val Ser Glu Gly Ala Gly Gly Leu His Ile Phe Ala Gly Asn
            370                 375                 380
Glu Val Ala Gly Ala Glu Gln Ser Gly Arg Ser Asp Gln Gly Ala Lys
385                 390                 395                 400
Glu Ile Arg Met Leu Val Ala Asp His Pro Gln Asn Gly Lys Asn Lys
            405                 410                 415
Glu Asn Glu Gly Tyr Val Gly Glu Ala Phe Ser Phe Ser Gly Lys Glu
            420                 425                 430
Gly Glu Asp Glu Arg Asp Asp Gln Lys Glu Gly Pro Thr Gly Ser Thr
            435                 440                 445
Gly Asp Gln Leu His Gly Lys Val Ser Ala Gly Ala Pro Asp Gly Val
            450                 455                 460
Asn Ser Lys Leu Met Pro Pro Ala Ser Val Met Thr Arg Leu Ile Leu
465                 470                 475                 480
Ile Met Val Trp Arg Lys Leu Ile Arg Asn Pro Asn Thr Tyr Ser Ser
            485                 490                 495
Leu Ile Gly Leu Ile Trp Ser Leu Ile Ser Phe Arg Trp His Val Ala
            500                 505                 510
Met Pro Lys Ile Ile Glu Lys Ser Ile Ser Ile Leu Ser Asp Ala Gly
            515                 520                 525
Leu Gly Met Ala Met Phe Ser Leu Gly Ile Phe Met Gly Leu Gln Pro
            530                 535                 540
Lys Met Ile Ala Cys Gly Asn Ser Val Ala Thr Phe Ala Met Ala Ile
545                 550                 555                 560
Arg Phe Leu Thr Gly Pro Ala Val Met Ala Ile Ala Ser Ile Ala Ile
            565                 570                 575
Gly Leu Arg Gly Thr Leu Leu Arg Val Ala Ile Val Gln Ala Ala Leu
            580                 585                 590
Pro Gln Gly Ile Val Pro Phe Val Phe Ala Lys Glu Tyr Asn Val His
            595                 600                 605
```

```
Pro Ala Ile Leu Ser Thr Gly Val Ile Phe Gly Met Leu Ile Ala Leu
    610                 615                 620

Pro Ile Thr Leu Leu Tyr Tyr Val Leu Leu Gly Leu
625                 630                 635

<210> SEQ ID NO 8
<211> LENGTH: 4
<212> TYPE: PRT
<213> ORGANISM: Unknown
<220> FEATURE:
<223> OTHER INFORMATION: Conserved region in plants

<400> SEQUENCE: 8

Gln Asn Gly Glu
1

<210> SEQ ID NO 9
<211> LENGTH: 4
<212> TYPE: PRT
<213> ORGANISM: Unknown
<220> FEATURE:
<223> OTHER INFORMATION: Conserved region in plants

<400> SEQUENCE: 9

Gln Asn Gly Asp
1

<210> SEQ ID NO 10
<211> LENGTH: 4
<212> TYPE: PRT
<213> ORGANISM: Unknown
<220> FEATURE:
<223> OTHER INFORMATION: Conserved region in plants

<400> SEQUENCE: 10

Gln Asn Gly Lys
1

<210> SEQ ID NO 11
<211> LENGTH: 4
<212> TYPE: PRT
<213> ORGANISM: Unknown
<220> FEATURE:
<223> OTHER INFORMATION: Conserved region in plants

<400> SEQUENCE: 11

Gln Asn Gly His
1

<210> SEQ ID NO 12
<211> LENGTH: 636
<212> TYPE: PRT
<213> ORGANISM: Cucumis sativus

<400> SEQUENCE: 12

Met Ile Ser Trp Lys Asp Leu Tyr Thr Val Leu Thr Ala Val Ile Pro
1               5                   10                  15

Leu Tyr Val Ala Met Ile Leu Ala Tyr Gly Ser Val Arg Trp Trp Lys
            20                  25                  30

Ile Phe Thr Pro Asp Gln Cys Ser Gly Ile Asn Arg Phe Val Ala Ile
        35                  40                  45

Phe Ala Val Pro Leu Leu Ser Phe His Phe Ile Ser Ser Asn Asp Pro
    50                  55                  60
```

-continued

```
Tyr Ala Met Asn Phe Arg Phe Ile Ala Ala Asp Thr Leu Gln Lys Ile
 65                  70                  75                  80

Ile Met Leu Phe Phe Leu Gly Ile Trp Thr Asn Phe Thr Lys Asn Gly
                 85                  90                  95

Ser Leu Glu Trp Met Ile Thr Ile Phe Ser Leu Ser Thr Leu Pro Asn
            100                 105                 110

Thr Leu Val Met Gly Ile Pro Leu Leu Ile Ala Met Tyr Gly Glu Tyr
        115                 120                 125

Ser Gly Ser Leu Met Val Gln Val Val Leu Gln Cys Ile Ile Trp
130                 135                 140

Tyr Thr Leu Leu Leu Phe Leu Phe Glu Tyr Arg Gly Ala Lys Ile Leu
145                 150                 155                 160

Ile Met Glu Gln Phe Pro Glu Thr Ala Ala Ser Ile Val Ser Phe Lys
                165                 170                 175

Val Asp Ser Asp Val Val Ser Leu Asp Gly Arg Asp Phe Leu Glu Thr
            180                 185                 190

Asp Ala Glu Ile Gly Asp Asp Gly Lys Leu His Val Thr Val Arg Lys
        195                 200                 205

Ser Asn Ala Ser Arg Arg Ser Leu Gly Pro Cys Ser Leu Pro Ala Leu
210                 215                 220

Thr Pro Arg Pro Ser Asn Leu Thr Gly Ala Glu Ile Tyr Ser Leu Ser
225                 230                 235                 240

Ser Ser Arg Asn Pro Thr Pro Arg Gly Ser Asn Phe Asn Asn Ser Asp
                245                 250                 255

Phe Tyr Ser Met Met Gly Phe Gln Gly Arg Leu Ser Asn Phe Gly Pro
            260                 265                 270

Gly Asp Leu Tyr Ser Val Gln Ser Ser Arg Gly Pro Thr Pro Arg Pro
        275                 280                 285

Ser Asn Phe Glu Glu Asn Ser Ala Val Gln Pro Gln Thr Ala Ser Pro
290                 295                 300

Arg Phe Gly Phe Tyr Pro Ala Gln Thr Val Pro Ser Ser Tyr Pro Ala
305                 310                 315                 320

Pro Asn Pro Glu Phe Thr Lys Thr Ala Lys Ile Pro Gln Pro Pro Pro
                325                 330                 335

Pro Pro Pro Pro Gln Gln Pro Gln Gln Gln Pro Gln Asn Ala Lys Pro
            340                 345                 350

Asn His Asp Ala Lys Glu Leu His Met Phe Val Trp Ser Ser Ser Ala
        355                 360                 365

Ser Pro Val Ser Glu Gly Ala Gly Gly Leu His Ile Phe Ala Gly Asn
370                 375                 380

Glu Val Ala Gly Ala Glu Gln Ser Gly Arg Ser Asp Gln Gly Ala Lys
385                 390                 395                 400

Glu Ile Arg Met Leu Val Ala Asp His Pro Gln Asn Gly Glu Asn Lys
                405                 410                 415

Glu Asn Glu Gly Tyr Val Gly Ala Phe Ser Phe Ser Gly Lys Glu
            420                 425                 430

Gly Glu Asp Glu Arg Asp Asp Gln Lys Glu Gly Pro Thr Gly Ser Thr
        435                 440                 445

Gly Asp Gln Leu His Gly Lys Val Ser Ala Gly Ala Pro Asp Gly Val
450                 455                 460

Asn Ser Lys Leu Met Pro Pro Ala Ser Val Met Thr Arg Leu Ile Leu
465                 470                 475                 480

Ile Met Val Trp Arg Lys Leu Ile Arg Asn Pro Asn Thr Tyr Ser Ser
```

```
                      485                 490                 495
Leu Ile Gly Leu Ile Trp Ser Leu Ile Ser Phe Arg Trp His Val Ala
                500                 505                 510

Met Pro Lys Ile Ile Glu Lys Ser Ile Ser Ile Leu Ser Asp Ala Gly
            515                 520                 525

Leu Gly Met Ala Met Phe Ser Leu Gly Ile Phe Met Gly Leu Gln Pro
        530                 535                 540

Lys Met Ile Ala Cys Gly Asn Ser Val Ala Thr Phe Ala Met Ala Ile
545                 550                 555                 560

Arg Phe Leu Thr Gly Pro Ala Val Met Ala Ile Ala Ser Ile Ala Ile
                565                 570                 575

Gly Leu Arg Gly Thr Leu Leu Arg Val Ala Ile Val Gln Ala Ala Leu
            580                 585                 590

Pro Gln Gly Ile Val Pro Phe Val Phe Ala Lys Glu Tyr Asn Val His
        595                 600                 605

Pro Ala Ile Leu Ser Thr Gly Val Ile Phe Gly Met Leu Ile Ala Leu
            610                 615                 620

Pro Ile Thr Leu Leu Tyr Tyr Val Leu Leu Gly Leu
625                 630                 635

<210> SEQ ID NO 13
<211> LENGTH: 649
<212> TYPE: PRT
<213> ORGANISM: Capsicum annuum

<400> SEQUENCE: 13

Met Ile Thr Trp His Asp Leu Tyr Val Val Leu Thr Ala Val Val Pro
1               5                   10                  15

Leu Tyr Val Ala Met Ile Leu Ala Tyr Gly Ser Val Arg Trp Trp Lys
            20                  25                  30

Ile Phe Ser Pro Asp Gln Cys Ser Gly Ile Asn Arg Phe Val Ala Ile
        35                  40                  45

Phe Ala Val Pro Leu Leu Ser Phe His Phe Ile Ser Leu Asn Asn Pro
    50                  55                  60

Tyr Glu Met Asn Phe Arg Phe Ile Ala Ala Asp Ser Leu Gln Lys Val
65                  70                  75                  80

Ile Met Leu Val Val Leu Ala Leu Trp Ala Asn Leu Thr Lys Asn Gly
                85                  90                  95

Ser Leu Glu Trp Ser Ile Thr Ile Phe Ser Leu Ser Thr Leu Pro Asn
            100                 105                 110

Thr Leu Val Met Gly Ile Pro Leu Leu Ile Ala Met Tyr Gly Glu Tyr
        115                 120                 125

Ser Gly Ser Leu Met Val Gln Val Val Leu Gln Cys Ile Ile Trp
    130                 135                 140

Tyr Thr Leu Leu Leu Phe Leu Phe Glu Tyr Arg Gly Ala Lys Met Leu
145                 150                 155                 160

Ile Met Glu Gln Phe Pro Glu Thr Ala Ala Ser Ile Val Ser Phe Lys
                165                 170                 175

Val Glu Ser Asp Val Val Ser Leu Asp Gly His Asp Phe Leu Glu Thr
            180                 185                 190

Asp Ala Glu Ile Gly Gln Asp Gly Lys Leu His Val Thr Val Arg Lys
        195                 200                 205

Ser Asn Ala Ser Arg Arg Ser Phe Ala Met Asp Asp Arg Pro Ser Asn
    210                 215                 220
```

```
Leu Thr Gly Ala Glu Ile Tyr Ser Leu Ser Ser Arg Asn Pro Thr
225                 230                 235                 240

Pro Arg Gly Ser Asn Phe Asn His Asn Asp Phe Tyr Ser Met Met Gly
            245                 250                 255

Phe Pro Gly Gly Arg Leu Ser Asn Phe Gly Pro Ala Asp Met Tyr Ser
        260                 265                 270

Val Gln Ser Ser Arg Gly Pro Thr Pro Arg Pro Ser Asn Phe Glu Glu
    275                 280                 285

Asn Cys Ala Pro Gly Gly Leu Val Gln Ser Ser Pro Arg Phe Gly Tyr
290                 295                 300

Phe Pro Ala Gln Gln Pro Ala Val Pro Gly Ser Tyr Pro Ala Pro Asn
305                 310                 315                 320

Pro Asp Ile Ala Ser Thr Val Pro Lys Ser Thr Lys Ile Gln Gln Pro
            325                 330                 335

Asn Val Gln Pro Gln Lys Gln Glu Gly Gln His His His Gln Gln Gln
            340                 345                 350

Gln Gln Pro Asn Ala Lys Ala Asn Asn His Asp Ala Lys Glu Leu His
        355                 360                 365

Met Phe Val Trp Ser Ser Asn Ser Pro Val Ser Glu Ala Gly Gly
370                 375                 380

Leu His Val Phe Gly Gly Asn Asp Phe Ser Ala Asn Glu Gln Ser Gly
385                 390                 395                 400

Arg Ser Asp Gly Ala Lys Glu Ile Arg Met Leu Val Ser Asp His Pro
                405                 410                 415

Gln Asn Gly Asp Thr Lys Gly Glu Phe Gly Gly Glu Asp Phe Thr Phe
            420                 425                 430

Gly Gly Ala Asn Gly Gly Gly Lys Asp Gly Asp Glu Lys Gly Asp
        435                 440                 445

Lys Glu Gly Pro Thr Gly Leu Thr Lys Leu Gly Ser Ser Ser Thr Ser
450                 455                 460

Glu Leu His Pro Lys Ile Gly Gly Gln Asp Val Gly Ile Gly Lys
465                 470                 475                 480

Gln Met Pro Pro Ala Ser Val Met Thr Arg Leu Ile Leu Ile Met Val
            485                 490                 495

Trp Arg Lys Leu Ile Arg Asn Pro Asn Thr Tyr Ser Ser Leu Ile Gly
                500                 505                 510

Leu Thr Trp Ser Leu Val Ser Phe Arg Trp Asp Val His Met Pro Lys
            515                 520                 525

Ile Ile Glu Lys Ser Ile Ser Ile Leu Ser Asp Ala Gly Leu Gly Met
530                 535                 540

Ala Met Phe Ser Leu Gly Leu Phe Met Ala Leu Gln Pro Lys Ile Ile
545                 550                 555                 560

Ala Cys Gly Asn Thr Val Ala Thr Phe Ala Met Ala Val Arg Phe Leu
            565                 570                 575

Thr Gly Pro Ala Val Met Ala Ala Ser Ile Ala Val Gly Leu Arg
        580                 585                 590

Gly Thr Leu Leu His Val Ala Ile Val Gln Ala Ala Leu Pro Gln Gly
            595                 600                 605

Ile Val Pro Phe Val Phe Ala Lys Glu Tyr Asn Val His Pro Ala Ile
        610                 615                 620

Leu Ser Thr Ala Val Ile Phe Gly Met Leu Ile Ala Leu Pro Ile Thr
625                 630                 635                 640

Leu Val Tyr Tyr Ile Ile Leu Gly Leu
```

-continued

```
                645

<210> SEQ ID NO 14
<211> LENGTH: 641
<212> TYPE: PRT
<213> ORGANISM: Citrullus lanatus

<400> SEQUENCE: 14

Met Ile Ser Trp Lys Asp Leu Tyr Thr Val Leu Thr Ala Val Ile Pro
1               5                   10                  15

Leu Tyr Val Ala Met Ile Leu Ala Tyr Gly Ser Val Arg Trp Trp Lys
            20                  25                  30

Ile Phe Thr Pro Asp Gln Cys Ser Gly Ile Asn Arg Phe Val Ala Ile
        35                  40                  45

Phe Ala Val Pro Leu Leu Ser Phe His Phe Ile Ser Ser Asn Asp Pro
    50                  55                  60

Tyr Ala Met Asn Phe Arg Phe Ile Ala Ala Asp Thr Leu Gln Lys Ile
65                  70                  75                  80

Ile Met Leu Phe Phe Leu Gly Ile Trp Thr Asn Phe Thr Lys Asn Gly
                85                  90                  95

Ser Leu Glu Trp Met Ile Thr Ile Phe Ser Leu Ser Thr Leu Pro Asn
            100                 105                 110

Thr Leu Val Met Gly Ile Pro Leu Leu Ile Ala Met Tyr Gly Glu Tyr
        115                 120                 125

Ser Gly Ser Leu Met Val Gln Val Val Leu Gln Cys Ile Ile Trp
    130                 135                 140

Tyr Thr Leu Leu Leu Phe Leu Phe Glu Tyr Arg Gly Ala Lys Ile Leu
145                 150                 155                 160

Ile Met Glu Gln Phe Pro Glu Thr Ala Ala Ser Ile Val Ser Phe Lys
                165                 170                 175

Val Asp Ser Asp Val Val Ser Leu Asp Gly Arg Asp Phe Leu Glu Thr
            180                 185                 190

Asp Ala Glu Ile Gly Asp Asp Gly Lys Leu His Val Thr Val Arg Lys
        195                 200                 205

Ser Asn Ala Ser Arg Arg Ser Leu Gly Pro Cys Ser Leu Pro Ala Leu
    210                 215                 220

Thr Pro Arg Pro Ser Asn Leu Thr Gly Ala Glu Ile Tyr Ser Leu Ser
225                 230                 235                 240

Ser Ser Arg Asn Pro Thr Pro Arg Gly Ser Asn Phe Asn His Ser Asp
                245                 250                 255

Phe Tyr Ser Met Met Gly Phe Gln Gly Arg Leu Ser Asn Phe Gly Pro
            260                 265                 270

Gly Asp Leu Tyr Ser Val Gln Ser Ser Arg Gly Pro Thr Pro Arg Pro
        275                 280                 285

Ser Asn Phe Glu Glu Asn Ser Ala Val Gln Pro Gln Thr Ala Ser Pro
    290                 295                 300

Arg Phe Gly Phe Tyr Pro Ala Gln Thr Val Pro Ser Ser Tyr Pro Ala
305                 310                 315                 320

Pro Asn Pro Glu Phe Thr Lys Thr Thr Ala Lys Ile Pro Gln Pro Pro
                325                 330                 335

Pro Pro Pro Pro Gln Gln Gln Pro Gln Pro Gln Pro Gln Asn Thr
            340                 345                 350

Lys Pro Asn His Asp Ala Lys Glu Leu His Met Phe Val Trp Ser Ser
        355                 360                 365
```

```
Ser Ala Ser Pro Val Ser Glu Gly Gly Gly Leu His Ile Phe Ala
    370             375             380

Gly Asn Glu Leu Ala Gly Ala Glu Gln Ser Gly Arg Ser Asp Gln Gly
385                 390                 395                 400

Ala Lys Glu Ile Arg Met Leu Val Ala Asp His Pro Gln Asn Gly Glu
            405                 410                 415

Asn Lys Gly Val Pro Glu Ser Glu Gly Tyr Val Gly Glu Ala Phe Ser
            420                 425                 430

Phe Ser Gly Lys Glu Gly Glu Glu Arg Asp Asp Gln Lys Glu Gly
        435                 440                 445

Pro Thr Gly Ser Thr Gly Asp Gln Leu Gln Gly Lys Val Ser Ala Gly
450                 455                 460

Ala Pro Asp Gly Gly Asn Ser Lys Leu Met Pro Pro Ala Ser Val Met
465                 470                 475                 480

Thr Arg Leu Ile Leu Ile Met Val Trp Arg Lys Leu Ile Arg Asn Pro
                485                 490                 495

Asn Thr Tyr Ser Ser Leu Ile Gly Leu Ile Trp Ser Leu Ile Ser Phe
            500                 505                 510

Arg Trp His Val Ala Met Pro Lys Ile Ile Glu Lys Ser Ile Ser Ile
        515                 520                 525

Leu Ser Asp Ala Gly Leu Gly Met Ala Met Phe Ser Leu Gly Ile Phe
530                 535                 540

Met Gly Leu Gln Pro Lys Met Ile Ala Cys Gly Asn Ser Val Ala Thr
545                 550                 555                 560

Phe Ala Met Ala Ile Arg Phe Leu Thr Gly Pro Ala Val Met Ala Ile
                565                 570                 575

Ala Ser Ile Ala Ile Gly Leu Arg Gly Thr Leu Leu Arg Val Ala Ile
            580                 585                 590

Val Gln Ala Ala Leu Pro Gln Gly Ile Val Pro Phe Val Phe Ala Lys
        595                 600                 605

Glu Tyr Asn Val His Pro Ala Ile Leu Ser Thr Gly Val Ile Phe Gly
    610                 615                 620

Met Leu Ile Ala Leu Pro Ile Thr Leu Leu Tyr Tyr Val Leu Leu Gly
625                 630                 635                 640

Leu

<210> SEQ ID NO 15
<211> LENGTH: 650
<212> TYPE: PRT
<213> ORGANISM: Solanum melongena

<400> SEQUENCE: 15

Met Ile Ser Trp His Asp Leu Tyr Val Val Leu Thr Ala Val Val Pro
1               5                   10                  15

Leu Tyr Val Ala Met Ile Leu Ala Tyr Gly Ser Val Arg Trp Trp Lys
            20                  25                  30

Ile Phe Ser Pro Asp Gln Cys Ser Gly Ile Asn Arg Phe Val Ala Ile
        35                  40                  45

Phe Ala Val Pro Leu Leu Ser Phe His Phe Ile Ser Leu Asn Asn Pro
50                  55                  60

Tyr Glu Met Asn Phe Arg Phe Ile Ala Ala Asp Ser Leu Gln Lys Val
65                  70                  75                  80

Ile Met Leu Val Val Leu Ala Leu Trp Ala Asn Phe Thr Lys Asn Gly
                85                  90                  95
```

```
Ser Leu Glu Trp Ser Ile Thr Ile Phe Ser Leu Ser Thr Leu Pro Asn
            100                 105                 110

Thr Leu Val Met Gly Ile Pro Leu Leu Ile Ala Met Tyr Gly Glu Tyr
            115                 120                 125

Ser Gly Ser Leu Met Val Gln Val Val Leu Gln Cys Ile Ile Trp
130                 135                 140

Tyr Thr Leu Leu Leu Phe Leu Phe Glu Tyr Arg Gly Ala Lys Met Leu
145                 150                 155                 160

Ile Met Glu Gln Phe Pro Glu Thr Ala Ala Ser Ile Val Ser Phe Lys
                165                 170                 175

Val Glu Ser Asp Val Val Ser Leu Asp Gly His Asp Phe Leu Glu Thr
            180                 185                 190

Asp Ala Glu Ile Gly Gln Asp Gly Lys Leu His Val Thr Val Arg Lys
            195                 200                 205

Ser Asn Ala Ser Arg Arg Ser Phe Ala Met Asp His Arg Pro Ser Asn
            210                 215                 220

Leu Thr Gly Ala Glu Ile Tyr Ser Leu Ser Ser Arg Asn Pro Thr
225                 230                 235                 240

Pro Arg Gly Ser Asn Phe Asn His Asn Asp Phe Tyr Ser Met Met Gly
                245                 250                 255

Phe Pro Gly Gly Arg Leu Ser Asn Phe Gly Pro Ala Asp Met Tyr Ser
                260                 265                 270

Val Gln Ser Ser Arg Gly Pro Thr Pro Arg Pro Ser Asn Phe Glu Glu
            275                 280                 285

Asn Cys Ala Pro Gly Ser Leu Val Gln Ser Ser Pro Arg Phe Gly Tyr
            290                 295                 300

Phe Pro Ala Gln Gln Pro Ala Pro Gly Ser Tyr Pro Ala Pro Asn Pro
305                 310                 315                 320

Glu Ile Ala Ser Thr Val Pro Lys Ser Thr Lys Pro Gln Gln Pro Asn
                325                 330                 335

Val Gln Ala Gln Lys Gln Glu Val Gln Gln Gln Gln Pro Pro Asn
            340                 345                 350

Ala Lys Gly Ile Asn His Asp Ala Lys Glu Leu His Met Phe Val Trp
            355                 360                 365

Ser Ser Ser Asn Ser Pro Val Ser Glu Ala Gly Gly Leu His Val Phe
370                 375                 380

Gly Gly Asn Asp Phe Ser Ala Asn Glu Gln Ser Gly Arg Ser Asp Gly
385                 390                 395                 400

Ala Lys Glu Ile Arg Met Leu Val Ser Asp His Pro Gln Asn Gly Asp
                405                 410                 415

Thr Lys Ala Ile Pro Gln Thr Gly Glu Phe Gly Gly Glu Asp Leu Thr
                420                 425                 430

Phe Arg Gly Ala Asn Gly Gly Lys Asp Gly Asp Glu Glu Lys Gly
            435                 440                 445

Glu Lys Glu Gly Pro Thr Gly Leu Thr Lys Leu Gly Ser Ser Ser Thr
            450                 455                 460

Ser Glu Leu His Pro Lys Ile Ala Gly Gly Gln Asp Val Asp Ile Gly
465                 470                 475                 480

Lys Gln Met Pro Pro Ala Ser Val Met Thr Arg Leu Ile Leu Ile Met
                485                 490                 495

Val Trp Arg Lys Leu Ile Arg Asn Pro Asn Thr Tyr Ser Ser Leu Ile
            500                 505                 510

Gly Leu Val Trp Ser Leu Ile Ala Phe Arg Trp His Val His Met Pro
```

```
            515                 520                 525
Lys Ile Ile Glu Lys Ser Ile Ser Ile Leu Ser Asp Ala Gly Leu Gly
530                 535                 540

Met Ala Met Phe Ser Leu Gly Leu Phe Met Ala Leu Gln Pro Lys Ile
545                 550                 555                 560

Ile Ala Cys Gly Asn Thr Val Ala Thr Phe Ala Met Ala Val Arg Phe
                565                 570                 575

Leu Thr Gly Pro Ala Val Met Ala Ala Ser Ile Ala Val Gly Leu
                580                 585                 590

Arg Gly Thr Leu Leu His Val Ala Ile Val Gln Ala Ala Leu Pro Gln
                595                 600                 605

Gly Ile Val Pro Phe Val Phe Ala Lys Glu Tyr Asn Val His Pro Ala
                610                 615                 620

Ile Leu Ser Thr Ala Val Ile Phe Gly Met Leu Ile Ala Leu Pro Ile
625                 630                 635                 640

Thr Leu Val Tyr Tyr Ile Ile Leu Gly Leu
                645                 650

<210> SEQ ID NO 16
<211> LENGTH: 653
<212> TYPE: PRT
<213> ORGANISM: Solanum lycopersicum

<400> SEQUENCE: 16

Met Ile Thr Trp His Asp Leu Tyr Val Val Leu Thr Ala Val Val Pro
1               5                   10                  15

Leu Tyr Val Ala Met Ile Leu Ala Tyr Gly Ser Val Arg Trp Trp Lys
                20                  25                  30

Ile Phe Ser Pro Asp Gln Cys Ser Gly Ile Asn Arg Phe Val Ala Ile
                35                  40                  45

Phe Ala Val Pro Leu Leu Ser Phe His Phe Ile Ala Met Asn Asn Pro
                50                  55                  60

Tyr Glu Met Asn Phe Arg Phe Ile Ala Ala Asp Ser Leu Gln Lys Val
65                  70                  75                  80

Ile Met Leu Val Val Leu Ser Leu Trp Ala Asn Leu Thr Lys Asn Gly
                85                  90                  95

Ser Leu Glu Trp Ser Ile Thr Ile Phe Ser Leu Ser Thr Leu Pro Asn
                100                 105                 110

Thr Leu Val Met Gly Ile Pro Leu Leu Ile Ala Met Tyr Gly Glu Tyr
                115                 120                 125

Ser Gly Ser Leu Met Val Gln Val Val Leu Gln Cys Ile Ile Trp
130                 135                 140

Tyr Thr Leu Leu Leu Phe Leu Phe Glu Tyr Arg Gly Ala Lys Met Leu
145                 150                 155                 160

Ile Met Glu Gln Phe Pro Glu Thr Ala Ala Ser Ile Val Ser Phe Lys
                165                 170                 175

Val Glu Ser Asp Val Val Ser Leu Asp Gly His Asp Phe Leu Glu Thr
                180                 185                 190

Asp Ala Glu Ile Gly Gln Asp Gly Lys Leu His Val Thr Val Arg Lys
                195                 200                 205

Ser Asn Ala Ser Arg Arg Ser Phe Ala Met Asp His Arg Pro Ser Asn
                210                 215                 220

Leu Thr Gly Ala Glu Ile Tyr Ser Leu Ser Ser Ser Arg Asn Pro Thr
225                 230                 235                 240
```

-continued

```
Pro Arg Gly Ser Asn Phe Asn His Asn Asp Phe Tyr Ser Met Met Gly
            245                 250                 255
Phe Pro Gly Gly Arg Leu Ser Asn Phe Gly Pro Ala Asp Met Tyr Ser
        260                 265                 270
Val Gln Ser Ser Arg Gly Pro Thr Pro Arg Pro Ser Asn Phe Glu Glu
    275                 280                 285
Asn Cys Ala Pro Gly Gly Leu Val Gln Ser Ser Pro Arg Phe Gly Tyr
290                 295                 300
Phe Pro Thr Gln Gln Pro Ala Pro Gly Ser Tyr Pro Ala Pro Asn Pro
305                 310                 315                 320
Glu Ile Ala Ser Ala Gly Pro Lys Ser Thr Lys Pro Gln Gln Pro Asn
                325                 330                 335
Val Gln Thr Gln Lys Gln Glu Val Gln Gln Gln Gln Gln His Gln
            340                 345                 350
Gln Pro Asn Ala Lys Ala Asn Asn His Asp Ala Lys Glu Leu His Met
        355                 360                 365
Phe Val Trp Ser Ser Asn Ser Pro Val Ser Glu Ala Gly Gly Leu
    370                 375                 380
His Val Phe Gly Gly Asn Asp Phe Ser Ala Asn Glu Gln Ser Gly Arg
385                 390                 395                 400
Ser Asp Gly Ala Lys Glu Ile Arg Met Leu Val Ser Asp His Thr Gln
                405                 410                 415
Asn Gly Asp Ser Lys Ala Ile Pro Gln Ile Gly Glu Phe Gly Gly Glu
            420                 425                 430
Asp Phe Thr Phe Gly Gly Ala Asn Gly Gly Lys Asp Gly Asp Glu
        435                 440                 445
Glu Lys Gly Glu Lys Glu Gly Pro Thr Gly Leu Thr Lys Leu Gly Ser
    450                 455                 460
Ser Ser Thr Ser Glu Leu His Pro Lys Leu Ala Gly Val Gln Asp Ala
465                 470                 475                 480
Gly Met Gly Lys Gln Met Pro Pro Ala Ser Val Met Thr Arg Leu Ile
                485                 490                 495
Leu Ile Met Val Trp Arg Lys Leu Ile Arg Asn Pro Asn Thr Tyr Ser
            500                 505                 510
Ser Leu Ile Gly Leu Ile Trp Ser Leu Ile Ser Phe Arg Trp His Val
        515                 520                 525
His Met Pro Lys Ile Ile Glu Lys Ser Ile Ser Ile Leu Ser Asp Ala
    530                 535                 540
Gly Leu Gly Met Ala Met Phe Ser Leu Gly Leu Phe Met Ala Leu Gln
545                 550                 555                 560
Pro Lys Ile Ile Ala Cys Gly Asn Thr Val Ala Thr Phe Ala Met Ala
                565                 570                 575
Val Arg Phe Leu Thr Gly Pro Ala Val Met Ala Ala Ser Ile Ala
            580                 585                 590
Val Gly Leu Arg Gly Thr Leu Leu His Val Ala Ile Val Gln Ala Ala
        595                 600                 605
Leu Pro Gln Gly Ile Val Pro Phe Val Phe Ala Lys Glu Tyr Asn Val
    610                 615                 620
His Pro Ala Ile Leu Ser Thr Ala Val Ile Phe Gly Met Leu Ile Ala
625                 630                 635                 640
Leu Pro Ile Thr Leu Val Tyr Tyr Ile Ile Leu Gly Leu
                645                 650
```

<210> SEQ ID NO 17
<211> LENGTH: 1911
<212> TYPE: DNA
<213> ORGANISM: Cucumis melo

<400> SEQUENCE: 17

```
atgatttcat ggaaggatct ttacaccgtc ttaacggcgg ttatccctct ttacgttgcc      60
atgattttgg cttacggttc tgttcggtgg tggaagattt tcactcccga tcaatgctct     120
ggaatcaatc gttttgttgc catttccgcc gttcctcttc tttcctttca ttttatatct     180
actaatgatc cttacgctat gaacttccgt ttcatcgctg ctgatacact tcagaagatt     240
attatgttgt tttttcttgg gatttggact aatttcacta agaatgggag tctggaatgg     300
atgattacta ttttctctct ctccaccctt ccgaataccc tggttatggg gattcctctg     360
ttgattgcca tgtacggtga gtacagtggg agtctgatgg tacaggtggt ggttttgcag     420
tgtattattt ggtacacgct tttgcttttt ctgtttgaat atcgtggtgc gaagattctc     480
attatggagc aatttcccga cggctgct tccattgttt cgtttaaagt tgattctgat      540
gtggtttcat tagatggtag agattttctt gagactgatg ctgagattgg agatgacgga     600
aagcttcacg tgacggtgag gaaatccaat gcttctcgtc gctctcttgg accttgttca     660
cttccggcat taacgcctag accttctaat ctcactggtg cggagattta tagcttgagt     720
tcttctcgaa accctactcc tcgtggctcc aatttcaacc attccgattt ctattctatg     780
atgggatttc aaggtcgatt gtctaacttc ggacctggag atttgtattc cgttcaatcc     840
tccagaggtc cgactcccg gccgtccaat tttgaagaga actatgccgt tcagcctcaa     900
actgcgtctc cgaggttcgg gttttacccg gctcaaactg tgccctcgtc ttacccggct     960
ccaaatcccg aattcactaa aaccgctaaa atccctcagc caccgccgcc tcctccgccg    1020
cagcaaccac agcaacaacc gcagaacgct aaaccaaacc atgacgcgaa ggagcttcac    1080
atgtttgttt ggagctctag cgcttcacca gtctctgaag gcgccggtgg acttcacatt    1140
ttcgccggga atgaagtagc cggagccgag caatctggac ggtccgatca aggcgccaag    1200
gagatccgga tgctcgtggc tgatcatcca caaaacgggg aaaacaaaga aaatgagggc    1260
tatgtaggtg aagccttag tttcagcggc aaagaagggg aagatgaaag agatgatcag    1320
aaagaaggac ccacaggctc aaccggagat caactccacg ggaaagtttc cgccggcgca    1380
ccggacggcg tgaactcaaa actaatgccg ccggcaagcg tgatgacccg tttgattcta    1440
atcatggttt ggcggaaact gatcagaaat cccaacacgt attcaagtct gatcggatta    1500
atttggtcgc tcatttcatt ccggtggcat gtggccatgc ctaaaataat agagaaatcg    1560
atctccatac tctctgatgc aggacttgga atggctatgt ttagcttagg tatatttatg    1620
ggactacaac caaagatgat agcatgtggc aactctgttg ctactttgc catggctatc    1680
agattcctaa ctgggccagc cgttatggct attgcttcca tcgctattgg cttacgcgga    1740
accctcctcc gcgttgctat tgttcaggcg gcattgcctc aaggaattgt accattcgtg    1800
tttgcaaaag agtacaacgt ccatccagct attctaagca ctggggttat ctttggaatg    1860
cttatagctc tccccattac tctgctctac tatgttctgc tgggtctgta a             1911
```

<210> SEQ ID NO 18
<211> LENGTH: 636
<212> TYPE: PRT
<213> ORGANISM: Cucumis melo

<400> SEQUENCE: 18

```
Met Ile Ser Trp Lys Asp Leu Tyr Thr Val Leu Thr Ala Val Ile Pro
1               5                   10                  15

Leu Tyr Val Ala Met Ile Leu Ala Tyr Gly Ser Val Arg Trp Trp Lys
            20                  25                  30

Ile Phe Thr Pro Asp Gln Cys Ser Gly Ile Asn Arg Phe Val Ala Ile
            35                  40                  45

Phe Ala Val Pro Leu Leu Ser Phe His Phe Ile Ser Thr Asn Asp Pro
        50                  55                  60

Tyr Ala Met Asn Phe Arg Phe Ile Ala Ala Asp Thr Leu Gln Lys Ile
65                  70                  75                  80

Ile Met Leu Phe Phe Leu Gly Ile Trp Thr Asn Phe Thr Lys Asn Gly
                85                  90                  95

Ser Leu Glu Trp Met Ile Thr Ile Phe Ser Leu Ser Thr Leu Pro Asn
            100                 105                 110

Thr Leu Val Met Gly Ile Pro Leu Leu Ile Ala Met Tyr Gly Glu Tyr
        115                 120                 125

Ser Gly Ser Leu Met Val Gln Val Val Leu Gln Cys Ile Ile Trp
    130                 135                 140

Tyr Thr Leu Leu Leu Phe Leu Phe Glu Tyr Arg Gly Ala Lys Ile Leu
145                 150                 155                 160

Ile Met Glu Gln Phe Pro Glu Thr Ala Ala Ser Ile Val Ser Phe Lys
                165                 170                 175

Val Asp Ser Asp Val Val Ser Leu Asp Gly Arg Asp Phe Leu Glu Thr
            180                 185                 190

Asp Ala Glu Ile Gly Asp Asp Gly Lys Leu His Val Thr Val Arg Lys
        195                 200                 205

Ser Asn Ala Ser Arg Arg Ser Leu Gly Pro Cys Ser Leu Pro Ala Leu
    210                 215                 220

Thr Pro Arg Pro Ser Asn Leu Thr Gly Ala Glu Ile Tyr Ser Leu Ser
225                 230                 235                 240

Ser Ser Arg Asn Pro Thr Pro Arg Gly Ser Asn Phe Asn His Ser Asp
                245                 250                 255

Phe Tyr Ser Met Met Gly Phe Gln Gly Arg Leu Ser Asn Phe Gly Pro
            260                 265                 270

Gly Asp Leu Tyr Ser Val Gln Ser Ser Arg Gly Pro Thr Pro Arg Pro
        275                 280                 285

Ser Asn Phe Glu Glu Asn Tyr Ala Val Gln Pro Gln Thr Ala Ser Pro
    290                 295                 300

Arg Phe Gly Phe Tyr Pro Ala Gln Thr Val Pro Ser Ser Tyr Pro Ala
305                 310                 315                 320

Pro Asn Pro Glu Phe Thr Lys Thr Ala Lys Ile Pro Gln Pro Pro Pro
                325                 330                 335

Pro Pro Pro Pro Gln Gln Pro Gln Gln Gln Pro Gln Asn Ala Lys Pro
            340                 345                 350

Asn His Asp Ala Lys Glu Leu His Met Phe Val Trp Ser Ser Ser Ala
        355                 360                 365

Ser Pro Val Ser Glu Gly Ala Gly Gly Leu His Ile Phe Ala Gly Asn
    370                 375                 380

Glu Val Ala Gly Ala Glu Gln Ser Gly Arg Ser Asp Gln Gly Ala Lys
385                 390                 395                 400

Glu Ile Arg Met Leu Val Ala Asp His Pro Gln Asn Gly Glu Asn Lys
                405                 410                 415

Glu Asn Glu Gly Tyr Val Gly Glu Ala Phe Ser Phe Ser Gly Lys Glu
```

-continued

```
                420             425             430
Gly Glu Asp Glu Arg Asp Asp Gln Lys Glu Gly Pro Thr Gly Ser Thr
        435             440             445

Gly Asp Gln Leu His Gly Lys Val Ser Ala Gly Ala Pro Asp Gly Val
        450             455             460

Asn Ser Lys Leu Met Pro Pro Ala Ser Val Met Thr Arg Leu Ile Leu
465             470             475             480

Ile Met Val Trp Arg Lys Leu Ile Arg Asn Pro Asn Thr Tyr Ser Ser
            485             490             495

Leu Ile Gly Leu Ile Trp Ser Leu Ile Ser Phe Arg Trp His Val Ala
            500             505             510

Met Pro Lys Ile Ile Glu Lys Ser Ile Ser Ile Leu Ser Asp Ala Gly
        515             520             525

Leu Gly Met Ala Met Phe Ser Leu Gly Ile Phe Met Gly Leu Gln Pro
        530             535             540

Lys Met Ile Ala Cys Gly Asn Ser Val Ala Thr Phe Ala Met Ala Ile
545             550             555             560

Arg Phe Leu Thr Gly Pro Ala Val Met Ala Ile Ala Ser Ile Ala Ile
            565             570             575

Gly Leu Arg Gly Thr Leu Leu Arg Val Ala Ile Val Gln Ala Ala Leu
            580             585             590

Pro Gln Gly Ile Val Pro Phe Val Phe Ala Lys Glu Tyr Asn Val His
        595             600             605

Pro Ala Ile Leu Ser Thr Gly Val Ile Phe Gly Met Leu Ile Ala Leu
        610             615             620

Pro Ile Thr Leu Leu Tyr Tyr Val Leu Leu Gly Leu
625             630             635
```

MODIFIED GENE RESULTING IN PARTHENOCARPIC FRUIT SET

RELATED APPLICATIONS AND INCORPORATION BY REFERENCE

This application is a Continuation-in-Part Application of International Patent Application Serial No. PCT/EP2016/051900 filed Jan. 29, 2016, which published as PCT Publication No. WO 2016/120438 on Aug. 4, 2016, which claims benefit of Netherlands Patent Application Serial No. 2014215 filed Jan. 30, 2015.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Aug. 29, 2017, is named 43104_00_2314_SL.txt and is 64,994 bytes in size.

FIELD OF THE INVENTION

The present invention relates to a modified gene which is capable of inducing parthenocarpy. The invention further relates to the use of the modified gene for inducing parthenocarpy in a plant, to methods for obtaining a modified gene, and to the use of markers to identify such a modified gene.

BACKGROUND OF THE INVENTION

The invention also relates to plants that have a modified gene which is capable of inducing parthenocarpy, as well as to methods for obtaining such plants and to methods for obtaining parthenocarpic fruits.

Usually a fruit is formed on a plant after pollination of the stigma and subsequent fertilization of the ovules. The success of pollination and fertilization which results in seed set and fruit development is regulated by a complex process in which various endogenous factors such as hormones, carbohydrates, and various enzymes play an important role. Key hormones that are known to be involved in this mechanism are for example cytokinins, abscisic acid, ethylene, auxins, brassinosteroids, and gibberellins. The relevance of each hormone can vary greatly between different plant species.

Seed set and fruit development are fundamental and closely interconnected plant processes. Fruit formation in most cases therefore requires fertilization as a trigger for initiation, and the endogenous factors that control and guide these processes are closely interacting. The rationale behind this dependency most likely is that a major function of the fruit is to protect the seeds and the embryos during their development. Moreover, the development of fruits takes a huge amount of energy, which would be biologically wasted if no seeds are developed. In addition, fruits serve as a way to facilitate the dispersal of mature seeds, when, for example, edible fruits are consumed by animals and humans.

Besides endogenous factors that affect seed set and fruit development, exogenous or environmental factors also play an important role. Extremities in temperature, drought, high amount of moisture, humidity, day length, and nutrient availability, as well as the presence of insects and diseases can influence proper flower development, gamete formation, pollination, fertilization, and fruit and seed development. A grower who depends on the number of fruits for a profitable yield can be faced with a reduction in income when any of these factors are sub-optimal. Since a lack of pollination, fertilization, and/or seed development in most crops will not result in fruit growth, favourable conditions during early fruit development are essential in obtaining an optimal yield.

In several crops it has been attempted to obtain fruits without seeds, as this is generally a highly desirable feature that is appreciated by consumers. Furthermore, the possibility to obtain seedless fruits can also be advantageous to growers as they become less dependent on environmental circumstances. Seedless fruits may also be a major advantage for the processing industry since no seeds need to be removed from the fruits during the processing procedure. Obviously the development of seedless fruits is not an easy target, as these fruits lack the fertilization and seed formation that are the commonly acknowledged triggers for the initiation of fruit development.

In some crops however this goal has been reached. For some crops it is possible to induce the development of parthenocarpic fruits through the exogenous application of growth regulators, such as auxin, cytokinin, or giberellic acid. This however has various negative aspects, as it increases costs, can result in deformation of the fruits or other defects, and is not always appreciated by consumers. In addition this exogenous induction of parthenocarpy will only work in certain crops.

One other way to obtain seedless fruits is by using triploids, which is the common method in for example banana and watermelon. This however complicates breeding since vegetative reproduction (banana) or the use of tetraploid parents (watermelon) is needed. In addition pollination is required in watermelon to induce fruit development.

Another option for obtaining seedless fruits is to use or modify a crop's genetic ability for parthenocarpy, which is the ability to set fruit without pollination or fertilization. This has been successfully exploited in cucumber, citrus, and certain types of grapes, and is also a possibility in tomato. When the stigma of a plant that has the capacity for facultative parthenocarpy is pollinated, the fruit will still set seeds, but without pollination seedless fruits will develop. In a plant with obligate parthenocarpy, even pollination will not result in seed set. When the goal of having parthenocarpy is to obtain fruits without seeds, rather than to obtain fruits under difficult environmental conditions, a means for preventing pollination has to be found. Preventing pollination can for example be reached by using all-female plants, self-incompatibility, or male sterility.

In certain crops the desire to develop seedless fruits has a high priority, but until now it has not been possible to accomplish this ambition by using a genetic basis. One of these crops is melon, *Cucumis melo*, which may comprise many fruit types. *Cucumis melo* plants show various sex expression phenotypes ranging from all female to all hermaphrodite, whereby the most common are monoecious and andromonoecious. Unfortunately, unlike in the related species *Cucumis sativus*, no natural parthenocarpy has been found. *Cucumis sativus* and *Cucumis melo* however cannot be crossed with each other to for example introgress the parthenocarpy from cucumber to melon.

Citation or identification of any document in this application is not an admission that such document is available as prior art to the present invention.

SUMMARY OF THE INVENTION

It is an object of the present invention to provide a genetic basis that leads to the induction of parthenocarpy in a plant.

During the research that led to the present invention a mutant *Cucumis melo* plant was produced that showed parthenocarpic fruit set. This parthenocarpy was found to be the result of a mutation in the PIN4 gene.

The invention thus relates to a modified PIN4 gene, the wild type of which is as identified in SEQ ID No. 1, encoding the protein of SEQ ID No. 5, or the wild type of which encodes a protein that has a sequence similarity of at least 80% to SEQ ID No. 5, which modified PIN4 gene encodes a protein that may comprise an amino acid change as a result of the modification, and which modified protein is capable of inducing parthenocarpic fruit set when present in a plant. The amino acid change is as compared to the wild type amino acid sequence of the protein.

In one embodiment the sequence similarity of the encoded wild type protein is in order of increased preference at least 80%, 81%, 82%, 83%, 84%, 85%, 86%, 87%, 88%, 89% 90%, 91%, 92%, 93%, 94%, 95%, 96%, 97%, 98%, 99%, 100%. The skilled person is familiar with methods for the calculation of sequence similarity. Suitably sequence similarity is calculated using the Sequence Identities And Similarities (SIAS) tool, which can be accessed at imed.med.ucm.es/Tools/sias. For similarity calculation the default similarity of amino acids as indicated in the diagram on said site was taken into account, using grouping of amino acids based on their physico-chemical properties.

The invention further relates to a modified PIN4 gene, the wild type of which encodes a protein as identified in SEQ ID No. 5, or SEQ ID No. 12, or SEQ ID No. 13, or SEQ ID No. 14, or SEQ ID No. 15, or SEQ ID No. 16, which modified gene encodes a modified protein that may comprise an amino acid change in the intracellular loop of the protein structure as a result of the modification, which altered protein is capable of inducing parthenocarpic fruit set when present in a plant.

The PIN-FORMED (PIN) protein family is a group of auxin efflux transport proteins that regulate the auxin efflux from the cell and are thus essential for temporal and spatial distribution of auxin during various processes in plant development. The PIN protein family has been studied in various crops, from which it became apparent that the PIN genes are involved in different developmental processes including embryogenesis, shoot and root morphogenesis, and tropic responses.

It was shown that silencing or down-regulation of orthologues of PIN genes can have different effects in different crop species. RNAi-mediated co-silencing of SlPIN3 and SlPIN4 in *Solanum lycopersicum* resulted in a strong effect on the vegetative phenotype of the plant, while no major effects on fruit development were found (Pattison and Catala, The Plant Journal (2012) 70, 585-598. Evaluating auxin distribution in tomato (*Solanum lycopersicum*) through an analysis of the PIN and AUX/LAX gene families.

Blackwell Publishing Ltd.). Another study showed that down-regulation of SlPIN4 expression, which is the most highly expressed PIN gene in *Solanum lycopersicum* ovaries and fruits, resulted in either obligate or facultative parthenocarpy (Mounet et al, Journal of Experimental Botany, 2012. Down-regulation of a single auxin efflux transport protein in tomato induces precocious fruit development. Available online at www.jxb.oxfordjournals.org). An earlier study indicated however that AtPIN1 or AtPIN3 mutants in *Arabidopsis*, which are established to be the PIN genes that are most highly expressed in *Arabidopsis* ovaries, did not lead to a parthenocarpic phenotype.

*Cucumis melo* is a crop in which parthenocarpic fruit set cannot readily be induced by the exogenous application of auxin. Therefore, it was not expected that a single mutation in an auxin efflux regulator would directly lead to the induction of parthenocarpic fruit set. The mutation that was identified according to the invention very surprisingly showed a remarkably nice parthenocarpic fruit set.

The present invention thus provides a modified PIN4 gene that when present in the genome leads to an amino acid change in its encoded protein, which modified protein leads to the induction of parthenocarpy when present in a plant.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIGS. 1A-E: Wild type gDNA (SEQ ID No. 1) and CDS (SEQ ID No. 2) sequences of the PIN4 gene of *Cucumis melo*.

Figure 5A:
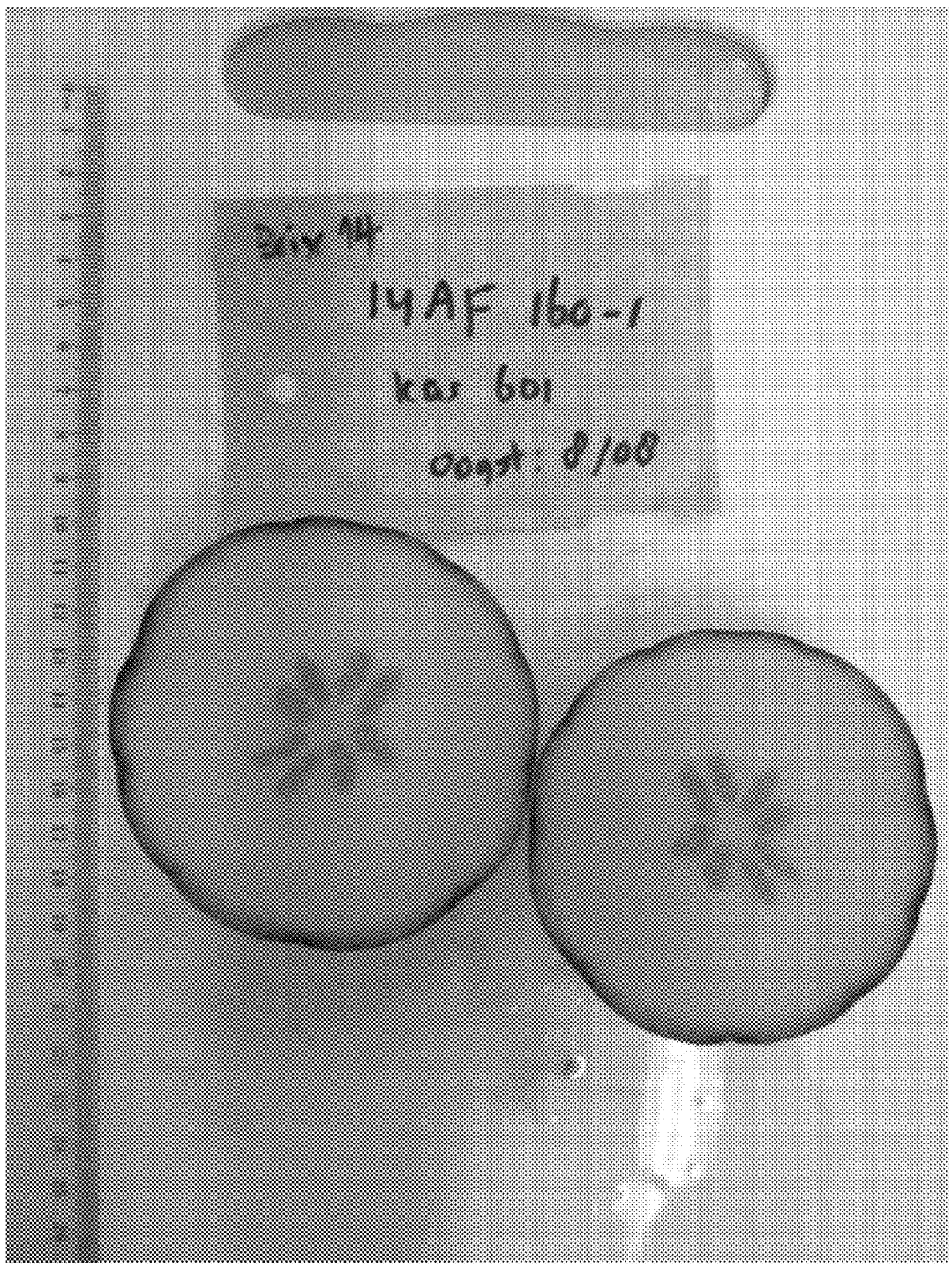

SEQ ID No. 3 shows the CDS that has the C to T SNP at position 497 (position 997 of the gDNA) of *Cucumis melo*.

SEQ ID No. 4 shows the CDS that has the G to A SNP at position 1240 (position 1740 of the gDNA) of *Cucumis melo*.

SEQ ID No. 17 shows the CDS that has the C to A SNP at position 884 (position 1384 of the gDNA) of *Cucumis melo*.

FIGS. 2A-B: Wild type protein sequence (SEQ ID No. 5) of the PIN4 protein of *Cucumis melo*. SEQ ID No. 6 gives the modified protein having a P to L amino acid change on position 166. SEQ ID No. 7 gives the modified protein having an E to K amino acid change on position 414. SEQ ID No. 18 gives the modified protein having an S to Y amino acid change on position 295.

FIGS. 3A-B: Protein sequences of the orthologous CmPIN4 proteins:

SEQ ID No. 12: *Cucumis sativus*; SEQ ID No. 13: *Capsicum annuum*; SEQ ID No. 14: *Citrullus lanatus*; SEQ ID No. 15: *Solanum melongena*; SEQ ID No. 16: *Solanum lycopersicum*.

FIGS. 4A-B: Aligned PIN4 protein sequences of *Cucumis melo* (melon)—SEQ ID No. 5; *Cucumis sativus* (cucumber)—SEQ ID No. 12; *Capsicum annuum* (pepper)—SEQ ID No. 13; *Citrullus lanatus* (watermelon)—SEQ ID No. 14; *Solanum melongena* (eggplant)—SEQ ID No. 15; *Solanum lycopersicum* (tomato)—SEQ ID No. 16.

The following symbols are used below the alignment:
*—all residues in that column are identical
:—conserved substitutions have been observed
.—semi-conserved substitutions have been observed
—no match (space)

Figure 5B:

FIGS. 5A-B: Seedless *Cucumis melo* fruit resulting from a *Cucumis melo* plant that has a modified PIN4 gene. FIG. 5a shows a fruit cut in half; FIG. 5b shows a slice of a seedless fruit.

FIG. 6: Sequence identity and sequence similarity of the wild type PIN4 proteins of *Cucumis melo* (melon)—SEQ ID No. 5; *Cucumis sativus* (cucumber)—SEQ ID No. 12; *Capsicum annuum* (pepper)—SEQ ID No. 13; *Citrullus lanatus* (watermelon)—SEQ ID No. 14; *Solanum melongena* (eggplant)—SEQ ID No. 15; *Solanum lycopersicum* (tomato)—SEQ ID No. 16. Sequence identity is calculated using a method taking the gaps into account; sequence similarity is based on grouping of amino acids that have similar properties. See SIAS method for both options.

DETAILED DESCRIPTION OF THE INVENTION

In this application the term "modification" or "modified" refers to a change in the coding sequence of the wild type PIN4 gene that leads to a modified or altered version of the wild type gene. The change in coding sequence in turn leads to an amino acid change in the encoded protein and therefore to a modified PIN4 protein. As used herein, "wild type" refers to the form of an organism, strain, gene, characteristic or trait as it would occur in nature, and is in contrast to the mutated or modified form for example.

PIN proteins can be divided into two types, commonly called 'long' and 'short' PIN proteins. The common structural feature of PIN proteins is the presence of two hydrophobic transmembrane domains that are separated by an intracellular hydrophilic loop. The length of the loop determines the PIN type, whereby the loop is much longer for the 'long' PIN proteins as compared to the 'short' PIN proteins.

The structure and sequence of the transmembrane domains is highly conserved amongst all PIN proteins. The sequence and structure of the loop however shows more variation, although also in the loop conserved stretches of amino acid residues can be identified. This conservation and variation is the basis for the clustering of PIN proteins into eight groups. PIN4 belongs to the 'long' PIN protein types, and is clustered in group 7, to which also PIN3 and PINT belong (Krecek et al, Genome Biology 2009, 10:249. The PIN-FORMED (PIN) protein family of auxin transporters. BioMed Central Ltd. Available online at genomebiology.com/2009/10/12/249).

In general, the intracellular loop of the PIN4 protein starts at about amino acid position 150 and ends at about amino acid position 500. The intracellular loop of SEQ ID No. 5 and SEQ ID Nos. 12-16 in particular starts at position 153. The intracellular loop of SEQ ID Nos. 5 and 12 ends at position 496. The intracellular loop of SEQ ID No. 14 ends at position 501, the intracellular loop of SEQ ID No. 13 ends at position 509, the intracellular loop of SEQ ID No. 15 ends at position 510, and the intracellular loop of SEQ ID NO. 16 ends at position 513.

During the research that led to the present invention a number of EMS induced SNP mutations was identified in the PIN4 gene of *Cucumis melo*. Five of the identified SNPs resulted in an amino acid change in the protein, and one resulted in a STOP codon (Table 1).

TABLE 1

PIN4 SNP mutations and the effect on the encoded PIN4 protein sequence.
Positions are as in the sequences of *Cucumis melo*, SEQ ID No. 1 (CmPIN4 genomic DNA (gDNA) wild type), SEQ ID No. 2 (CmPIN4 coding DNA sequence (CDS) wild type) and SEQ ID No. 5 (CmPIN4 protein wild type)

| | | | Mutation information | | | | |
|---|---|---|---|---|---|---|---|
| Plant ID | WGS Name | Nt change | Mutation position on gDNA | Mutation position on CDS | Mutation Type | Codon Change | AAchange_pos |
| 320 | RZgene03_PIN4_g59516 | C-T | 997 | 497 | AAchange | cCc/cTc | P166L |
| 323 | RZgene03_PIN4_g59516 | G-A | 1060 | 560 | AAchange | aGa/aAa | R187K |
| 363 | RZgene03_PIN4_g59516 | C-A | 1384 | 884 | AAchange | tCt/tAt | S295Y |
| 404 | RZgene03_PIN4_g59516 | C-T | 1606 | 1106 | AAchange | tCa/tTa | S369L |

TABLE 1-continued

PIN4 SNP mutations and the effect on the encoded PIN4 protein sequence.
Positions are as in the sequences of *Cucumis melo*, SEQ ID No. 1 (CmPIN4 genomic DNA
(gDNA) wild type), SEQ ID No. 2 (CmPIN4 coding DNA sequence (CDS) wild type) and SEQ
ID No. 5 (CmPIN4 protein wild type)

| | | | Mutation information | | | | |
|---|---|---|---|---|---|---|---|
| Plant ID | WGS Name | Nt change | Mutation position on gDNA | Mutation position on CDS | Mutation Type | Codon Change | AAchange_pos |
| 431 | RZgene03_PIN4_g59516 | G-A | 1740 | 1240 | AAchange | Gaa/Aaa | E414K |
| 527 | RZgene03_PIN4_g59516 | C-T | 3171 | 1765 | STOP | Cag/Tag | Q589* |

Phenotyping of *C. melo* plants which may comprise these and other SNP mutations was performed in the greenhouse (Example 2). Pollination was prevented, to be able to observe parthenocarpic fruit set. It was initially observed that two of the induced SNPs that are listed in Table 1 resulted in parthenocarpic fruit set in the absence of pollination. Parthenocarpic fruit set was found in the plant having ID 320, which comprised the C to T SNP on position 997 of the gDNA, corresponding to position 497 of the CDS, and for the plant having ID 431, which comprised the G to A SNP on position 1740 of the gDNA, corresponding to position 1240 of the CDS. During subsequent phenotyping, parthenocarpic fruit set was also found in the plant having ID 363, which comprises a C to A SNP on position 1384 of the gDNA, corresponding to position 884 of the CDS (Table 1; FIGS. 1A-E, SEQ ID Nos. 3 and 4, and SEQ ID No. 17).

Said C to T SNP results in an amino acid change from proline (P) to leucine (L) on position 166 of the wild type CmPIN4 protein. Said G to A SNP results in an amino acid change from glutamic acid (E) to lysine (K) on position 414 of the wild type CmPIN4 protein. Said C to A SNP results in an amino acid change from serine (S) to tyrosine (Y) on position 295 of the wild type CmPIN4 protein (FIG. 2A-B, SEQ ID Nos. 5-7 and SEQ ID No. 18).

In one embodiment the invention provides a modified PIN4 gene that has an amino acid change in the intracellular loop of the PIN4 protein as a result of the modification, which altered protein leads to the induction of parthenocarpy in a plant. The invention also relates to the modified protein of said modified PIN4 gene.

In one embodiment the amino acid change in the protein is a change that results in a modification of the structure of the loop of the PIN4 protein, which modified protein structure leads to the induction of parthenocarpy in a plant. The modified protein structure is expected to affect the functionality of the protein, thereby resulting in the induction of parthenocarpy.

In a particular embodiment the amino acid change in the protein is a change from an uncharged or a negatively charged amino acid to a positively charged amino acid.

In another embodiment the amino acid change in the protein is a change from an uncharged non-hydrophobic amino acid to a hydrophobic amino acid.

Certain amino acid substitutions produce a conservative change, which means they result in a functionally equivalent protein. Conservative amino acid substitutions may be made on the basis of chemical properties, for example similarity in polarity, charge, solubility, hydrophobicity, hydrophilicity or the amphipathic nature of the residues, in which case the resulting protein may still function normally. The amino acid substitution may occur in a region of the protein that does not significantly affect the protein structure or function. Conversely, an amino acid substitution that occurs at a well conserved or invariant position that is essential for the structure and/or function of the protein, or substitutions with amino acids that do not share conserved chemical properties (e.g. hydrophobic vs. charged vs. polar), may lead to non-conservative amino acid changes.

During the research for this invention, the protein modifications that were identified and resulted in parthenocarpic fruit set comprised an amino acid change in the intracellular loop of the protein structure. The two other amino acid substitutions are located in the protein loop as well, but appear to have resulted in a conservative change, which has not led to the induction of parthenocarpy.

The amino acid change from P to L at position 166 of the CmPIN4 protein leads to the alteration of a highly conserved amino acid at this position. This amino acid is positioned at the beginning of the loop structure, and proline is known to be an important factor in protein structure determination. An amino acid change at this position is highly likely to result in a change of the protein structure, more specifically in this case in the structure of the intracellular loop.

The amino acid change from S to Y at position 295 of the CmPIN4 protein leads to the modification of a conserved amino acid at the end of a highly conserved amino acid stretch in this region. The modification is a change from a polar uncharged amino acid to a hydrophobic amino acid.

In addition, the amino acid change from E to K at protein position 414 of the CmPIN4 protein is distinctive from the other amino acid changes from Table 1 since the amino acids involved in this modification are found to have oppositely charged residues. As a result of this the charge of the amino acid at this position has changed from negative (E) to positive (K). A change in charge in the loop or in this area in the loop is also very likely to have an effect on the 3D structure of the intracellular loop of the PIN4 protein.

The loop is the main part of a PIN protein that establishes the interaction with substrates or other proteins to perform its function in the various developmental processes in which it is involved. A minor change in this structure is not expected to directly lead to down-regulation or silencing of gene expression or activity. It is however very probable that a change in loop-structure affects the function of the protein, for example in substrate recognition or interaction with other proteins in downstream processes. Without wishing to be bound by theory, it is therefore expected that in the identified mutants a change in this loop-structure has led to an alteration in protein function, which alteration has resulted in the induction of parthenocarpy. The alteration in protein function could for example have led to an accumulation of auxin in the ovaries which stimulates fruit development.

Among the amino acids, lysine (K), histidine (H), and arginine (R) are positively charged. The negatively charged amino acids are glutamic acid (E) and aspartic acid (D); all other amino acids have no charge. When a negatively charged amino acid, i.e. E or D, or a non-charged amino acid, within the intracellular loop of a PIN4 protein is altered into a positively charged amino acid, i.e. K, H, or R, it is predicted to result in a change of structure within the protein loop. The structure change affects the protein function, which in a plant of the invention results in the induction of parthenocarpy.

In one embodiment the amino acid change of the protein of the invention is attained by a single SNP in the PIN4 gene, and is in particular a change from proline (P) to leucine (L), or a change from glutamic acid (E) to lysine (K), or a change from serine (S) to tyrosine (Y).

As mentioned earlier, the structure of the transmembrane domains is highly conserved within all PIN proteins. The sequence and structure of the loop however also shows conserved stretches. Identification of PIN4 orthologues in different crops and a multiple sequence alignment of PIN proteins has revealed that the amino acids that were modified in this invention are indeed highly conserved over all known orthologous PIN proteins (results not shown), and in particular over all PIN4 proteins.

Further examination of the region of positions 411 to 414 of SEQ ID No. 5, reveals that the corresponding regions of all orthologous PIN4 proteins contain a QNGE (Table 2, SEQ ID No. 8) or QNGD (SEQ ID No. 9) amino acid stretch, which means that the charge on position 414 or the corresponding position in an orthologous protein is always negative. An amino acid change in this stretch from E or D to a positively charged amino acid, preferably from E to K (SEQ ID No. 10) or from D to H (SEQ ID No. 11), will therefore result in a change in the tertiary structure in this area of the protein.

TABLE 2

PIN4 wild type and modified amino acid sequence stretch resulting in parthenocarpy

| Conserved amino acid stretch in the loop of PIN4 proteins | |
| --- | --- |
| QNGE | SEQ ID No. 8 |
| QNGD | SEQ ID No. 9 |
| Modified amino acid stretch resulting in parthenocarpy | |
| QNGK | SEQ ID No. 10 |
| QNGH | SEQ ID No. 11 |

The invention in one embodiment therefore relates to a PIN4 protein that has an amino acid change from E to K or from D to H in the highly conserved QNGE or QNGD amino acid stretch of the intracellular loop, which altered protein leads to the induction of parthenocarpy when present in a plant. The QNGE or QNGD stretch is preferably as found at positions 411-414 of SEQ ID No. 5, whereby E is at position 414, or on the corresponding positions of the orthologous proteins having SEQ ID Nos. 12-16 (FIG. 3). Corresponding positions are as follows: positions 411-414 of SEQ ID No. 12; positions 417-420 of SEQ ID No. 13; positions 413-416 of SEQ ID No. 14; positions 413-416 of SEQ ID No. 15; positions 416-419 of SEQ ID No. 16. The position of E or D respectively in those proteins therefore relates to 414 in SEQ ID No. 12; 420 in SEQ ID No. 13; 416 in SEQ ID No. 14; 416 in SEQ ID No. 15; 419 in SEQ ID No. 16 (Table 3).

In another embodiment the invention relates to a non-conservative amino acid substitution of proline (P), preferably of proline at position 166 of the CmPIN4 protein of SEQ ID No. 5, or at position 166 of an orthologous protein as presented in SEQ ID Nos. 12-16. Preferably this conserved proline is substituted with leucine, or any other non-conservative amino acid change which would modify the structure and/or the functionality of the encoded PIN4 protein. The skilled person is familiar with substitutions which would be non-conservative amino acid changes for a given amino acid.

Further analysis of the amino acid region of the mutation S to Y at position 295 of SEQ ID No. 5, revealed that in orthologous PIN4 protein sequences in this region an almost identical stretch of amino acids is found which ends with either SA, in SEQ ID Nos. 5, 12, and 14, or CA in SEQ ID Nos. 13, 15, and 16. In SEQ ID Nos. 5, 12, and 14 serine (S) is found at position 295. In SEQ ID Nos. 13, 15, and 16 cysteine (C) is found at position 290 of the protein.

In one embodiment the invention relates to a mutation leading to a non-conservative amino acid substitution of serine (S) at position 295 of SEQ ID Nos. 5, 12, or 14; or of cysteine (C) at position 290 of SEQ ID Nos. 13, 15, or 16. The substitution is preferably with an amino acid having different chemical properties, such as a hydrophobic or charged amino acid. In a particular embodiment the mutation leads to a substitution with tyrosine (Y).

TABLE 3

PIN4 proteins and examples of positions for mutations resulting in parthenocarpic fruit set

| PIN4 protein SEQ ID | crop | position P | position QNGE or QNGD stretch | position E or D | position S or C |
| --- | --- | --- | --- | --- | --- |
| SEQ ID No. 5 | Cucumis melo | 166 | 411-414 | 414 | 295 |
| SEQ ID No. 12 | Cucumis sativus | 166 | 411-414 | 414 | 295 |
| SEQ ID No. 13 | Capsicum annuum | 166 | 417-420 | 420 | 290 |
| SEQ ID No. 14 | Citrullus lanatus | 166 | 413-416 | 416 | 295 |
| SEQ ID No. 15 | Solarium melongena | 166 | 413-416 | 416 | 290 |
| SEQ ID No. 16 | Solanum lycopsersicum | 166 | 416-419 | 419 | 290 |

The invention for the first time links genetic modifications of the PIN4 gene per se to the induction of parthenocarpic fruit set. While the PIN4 mutations that have been identified in the course of this research illustrate the causative effect between the aforementioned mutations of the CmPIN4 gene and the trait of the invention, these are certainly not the only mutations of the PIN4 gene that would lead to the trait of the invention and the invention should thus not be limited to these specific mutations but extends to all other modifications, in particular mutations, of the DNA sequence of the PIN4 gene itself that lead to the same effect of parthenocarpic fruit set when expressed in a plant.

The present invention is broadly applicable to all plant species and crops that harbour a functional homologue of CmPIN4 gene in their genome, i.e. a homologue that performs the same or a similar biological function. Identification of PIN4 orthologues, i.e. PIN4 genes in other species, can be performed in many crops, methods for which are known in the art. In the present research, a Basic Local Alignment Search Tool (BLAST) program was used to compare the *Cucumis melo* PIN4 DNA and protein sequence against sequences of other plant genomes. This resulted in the identification of a number of candidate PIN4 orthologous genes. For some plant species, orthologous PIN4 protein sequences were identified by Blast X or Blast P as reciprocal best hits to the *Cucumis melo* PIN4 protein sequence. Protein sequences of the PIN4 orthologues were identified through this method. Multiple sequence alignments of the protein sequences using CLUSTAL confirmed that these were orthologous PIN4 proteins (FIGS. 4A-B).

In one embodiment, the invention relates to modified versions of the PIN4 genes of *Cucumis melo, Cucumis sativus, Citrullus lanatus, Solanum lycopersicum, Solanum melongena*, or *Capsicum annuum*, whereby the modified version of the PIN4 gene leads to a modified PIN4 protein. In particular, the invention relates to a modified PIN4 gene of *Cucumis melo*. Once the DNA sequences of orthologous PIN4 genes and their encoded PIN4 proteins are known, this information may be used to modulate or modify the proteins encoded by said genes using the methods described herein.

In one embodiment the invention relates to a plant which may comprise the modified PIN4 gene as disclosed herein, which plant shows parthenocarpic fruit set as a result of the presence of the modified PIN4 protein. The modified PIN4 gene can be present in heterozygous or homozygous form.

In one embodiment the plant which may comprise the modified PIN4 gene and/or the modified PIN4 protein of the invention, and showing parthenocarpic fruit set, is a plant of the species *Cucumis melo, Cucumis sativus, Citrullus lanatus, Solanum lycopersicum, Solanum melongena*, or *Capsicum annuum*. Preferably a plant of the invention is a *Cucumis melo* plant.

Optionally, a modification of the PIN4 gene and/or PIN4 protein as herein described may be combined with one another, or with another modification in the same gene or in another gene to obtain the parthenocarpic phenotype.

Parthenocarpy or parthenocarpic fruit set as used herein in relation to a plant of the invention is fruit set that occurs without the need for pollination. After pollination a plant of the invention preferably does develop viable seeds in the fruit. The parthenocarpy of the invention is a form of facultative parthenocarpy, which is advantageous because it allows for seed production to occur upon pollination. The capability of parthenocarpic fruit set means that the plant can develop a parthenocarpic fruit when a flower is not pollinated, but can develop a regular fruit with seeds after pollination has taken place.

Pollination can be prevented in various ways. From hermaphrodite, or 'perfect', flowers, as well as from male flowers, the anthers can be emasculated. Male flowers can also be partly or completely removed to result in non-functionality of the anthers. Alternatively male sterility can be used or induced, which can be genetic male sterility, cytoplasmic male sterility, positional or functional male sterility, or any other alternative resulting in male sterility.

For female flowers on gynoecious, i.e. all-female, plants, care has to be taken that no plants of the same species with viable pollen are in the vicinity, and/or no pollinating insects are around. In a particular situation the female flowers or plants can be enclosed or grown in a protected environment so that no pollen can reach the stigma to result in pollination and fertilization. In monoecious plants, which have separate male and female flowers, female flowers can be covered or closed to prevent pollination, or male flowers can be emasculated or removed.

The invention further provides a *Cucumis melo* plant which may comprise a modified PIN4 gene and PIN4 protein as disclosed herein, wherein the female flowers set fruit without pollination. In a particular embodiment the anthers or male flowers do not develop or abort before full flowering.

In one embodiment the invention relates to a *Cucumis melo* plant which may comprise a modified PIN4 gene, whereby the modification results in a modified PIN4 protein, in particular a PIN4 protein that has a non-conservative modification in the intracellular loop, which modification results in the capability of parthenocarpic fruit set.

In one embodiment the invention relates to a *Cucumis melo* plant that is capable of parthenocarpic fruit set as a result of a SNP in the PIN4 gene at position 497 or position 1240 or position 884 of SEQ ID No. 2, in particular a C to T SNP at position 497, or a G to A SNP at position 1240, or a C to A SNP at position 884.

In one embodiment the invention relates to a *Cucumis melo* plant that is capable of parthenocarpic fruit set as a result of a PIN4 protein that has a modification at position 166 or position 295 or position 414 of SEQ ID No. 5, in particular a modification from P to L at position 166 represented by SEQ ID No. 6, or a modification from S to Y at position 295 represented by SEQ ID No. 18, or a modification from E to K at position 414 represented by SEQ ID No. 7.

The invention also relates to the use of a modified PIN4 gene of the invention for the induction of parthenocarpy in a plant, in particular in a plant of the species *Cucumis melo, Cucumis sativus, Citrullus lanatus, Solanum lycopersicum, Solanum melongena*, or *Capsicum annuum*, more particular in a *Cucumis melo* plant.

A modified PIN4 gene can be introgressed from a plant comprising the modified PIN4 gene into a plant lacking the modified PIN4 gene but having other desired traits, using crossing when the plants are sexually compatible, optionally combined with techniques that aid the development of viable seeds or facilitate development into a plant. Use of the modified PIN4 gene of the invention may comprise use by introgressing the gene from a donor plant which may comprise the modified PIN4 gene and having the capability for parthenocarpic fruit set, into a recipient plant that lacks the modified PIN4 gene. The introgression of the modified PIN4 gene leads to the capability for parthenocarpic fruit set in the recipient plant.

In a particular embodiment, a modified PIN4 gene can be introgressed from a *Cucumis melo* plant which may comprise the modified PIN4 gene as disclosed herein into a *Cucumis melo* plant lacking the modified PIN4 gene using standard breeding techniques.

Selection for plants that have obtained the parthenocarpic trait of the invention from a plant carrying the modified PIN4 gene is started in the F1 or any further generation from a cross between the recipient plant and a donor plant, suitably by using a molecular marker that is based upon the modification to the PIN4 gene that underlies the trait. The skilled person is familiar with creating and using molecular markers to identify such modifications. In a particular embodiment examples of suitable molecular markers are markers to identify the SNP C997>T997 or the SNP G1740>A1740 or the SNP C1384>A1384 in the PIN4 gene of *Cucumis melo* according to SEQ ID No. 1. Such a marker can be a SNP marker which may comprise the SNP that is to be identified, or any other molecular marker that the skilled person can design based on a modification of the genome that underlies the trait. Other routinely used molecular markers for the identification of variation or modifications of the genome are for example, but not limited to, RFLPs, SSLPs, AFLPs, RAPDs, VNTRs, SSRs, STRs, DArTs, and RAD markers.

The invention also relates to the use of a molecular marker to identify a modification in a PIN4 gene which leads to the capability of parthenocarpic fruit set in a plant, preferably a marker to identify a SNP corresponding to a nucleotide substitution at position 497 or position 1240 or position 884 of SEQ ID No. 2, or to identify a SNP resulting in an amino acid substitution at position 166 or position 414 or position 295 of SEQ ID No. 5, or a marker to identify a SNP resulting in an amino acid substitution at the corresponding positions of SEQ ID Nos. 12-16. Such a marker can be a molecular marker which may comprise the SNP that is to be identified, or another marker that the skilled person can easily design when the position of the modification to be identified is known. In a particular embodiment the invention relates to the use of a marker based on or which may comprise SNP C997>T997 or SNP G1740>A1740 or SNP C1384>A1384 of the CmPIN4 gene, or based on or which may comprise corresponding SNPs on corresponding positions of orthologous genes as identified herein, encoding the proteins of SEQ ID Nos. 12-16.

Alternatively, selection for the modified PIN4 gene is started in the F2 or any further generation of a cross or alternatively of a backcross. Selection of plants in the F2 can optionally be done phenotypically based on the observation of parthenocarpic fruit set, as well as by using a molecular marker(s) which directly or indirectly detect(s) the modification of the PIN4 gene that underlies the trait.

Selection for plants having the modified PIN4 gene, which when heterozygously or homozygously present leads to the induction of parthenocarpic fruit set, can also be started in the F3 or a later generation.

Crossing can optionally be followed by embryo rescue techniques or other techniques that result in a successful combination and introgression, which techniques are known to the person skilled in the art.

The invention also relates to a fruit produced by a plant of the invention, which plant may comprise the modified PIN4 gene as disclosed herein. The fruit is suitably a seedless fruit, which has developed on a plant of the invention without pollination, or alternatively a seeded fruit that has developed on a plant of the invention after pollination has taken place. The seeds of this fruit still comprise the modified PIN4 gene of the invention and therefore also form a part of the invention.

As used herein a seedless fruit is a fruit that has developed without pollination having taken place, and therefore no viable seeds have formed in the fruit. In some instances some rudimentary seeds can be observed, but since these are not fertilized, as no pollination took place, these are not properly developed seeds and will not germinate when sown.

The invention further relates to a method for the production of a seedless fruit, in particular a seedless *Cucumis melo* fruit, which may comprise providing a plant having a modified PIN4 gene that leads to the capability of parthenocarpic fruit set, growing said plant, and allowing the fruit to develop without pollination. The produced fruit and parts of the fruit, optionally in processed form, are also part of this invention.

The invention also relates to the use of a plant of the invention that may comprise a modified PIN4 gene for the production of seedless fruits, in particular for the production of seedless *Cucumis melo* fruits.

The invention also relates to the use of a plant of the invention that may comprise a modified PIN4 gene as a source of propagating material.

The invention also relates to the use of a plant of the invention that may comprise a modified PIN4 gene in plant breeding.

The invention furthermore relates to a cell of a plant as claimed. Such cell may be either in isolated form or may be part of the complete plant or parts thereof and then still constitutes a cell of the invention because such a cell harbours the modified PIN4 gene that leads to the induction of parthenocarpy. Each cell of a plant of the invention carries the genetic information that leads to induction of parthenocarpy. Such a cell of the invention may also be a regenerable cell that can be used to regenerate a new plant of the invention.

The invention also relates to tissue of a plant as claimed. The tissue can be undifferentiated tissue or already differentiated tissue. Undifferentiated tissues are for example stem tips, anthers, petals, pollen and can be used in micropropagation to obtain new plantlets that are grown into new plants of the invention. The tissue can also be grown from a cell of the invention.

The invention according to a further aspect thereof relates to seed, wherein the plant that can be grown from the seed is a plant of the invention, which may comprise the modified PIN4 gene that leads to the induction of parthenocarpy. The invention also relates to seeds of a plant as claimed, which can be obtained after pollination. The seeds harbour the modified PIN4 gene that, when a plant is grown from the seeds, makes this plant a plant of the invention.

The invention also relates to progeny of the plants, cells, tissues and seeds of the invention, which progeny may comprise the modified PIN4 gene that leads to the induction of parthenocarpy. Such progeny can in itself be plants, cells, tissues, or seeds.

As used herein the word 'progeny' is intended to mean the first and all further descendants from a cross with a plant of the invention that has a modified PIN4 gene that leads to the capability of parthenocarpic fruit set.

'Progeny' also encompasses plants that carry the modified PIN4 gene of the invention and have the trait of the invention, and are obtained from other plants or progeny of plants of the invention by vegetative propagation or multiplication. Progeny of the invention suitably comprises the modified PIN4 gene and the modified PIN4 protein and the trait of the invention.

The trait of the invention as used herein is the capability of parthenocarpic fruit set without pollination as a result of the presence of a modified PIN4 gene and/or a modified PIN4 protein.

The invention thus further relates to parts of a claimed plant that are suitable for sexual reproduction. Such parts are for example selected from the group consisting of microspores, pollen, ovaries, ovules, embryo sacs, and egg cells. In addition, the invention relates to parts of a claimed plant that are suitable for vegetative reproduction, which are in particular cuttings, roots, stems, cells, protoplasts. The parts of the plants as mentioned above are considered propagation material. The plant that is produced from the propagation material may comprise the modified PIN4 gene that leads to the capability of parthenocarpic fruit set.

According to a further aspect thereof the invention provides a tissue culture of a plant carrying the modified PIN4 gene of the invention, which is also propagation material. The tissue culture may comprise regenerable cells. Such tissue culture can be selected or derived from any part of the plant, in particular from leaves, pollen, embryos, cotyledon, hypocotyls, meristematic cells, roots, root tips, anthers, flowers, seeds, and stems. The tissue culture can be regenerated into a plant carrying the modified PIN4 gene of the invention, which regenerated plant expresses the trait of the invention and is also part of the invention.

The invention furthermore relates to hybrid seed and to a method for producing such hybrid seed which may comprise crossing a first parent plant with a second parent plant and harvesting the resultant hybrid seed, wherein said first parent plant and/or said second parent plant has the modified PIN4 gene of the invention. The resulting hybrid plant that comprises the modified PIN4 gene of the invention and which shows the trait of the invention is also a plant of the invention.

In one embodiment the plant of the invention which may comprise the modified PIN4 gene either homozygously or heterozygously is a plant of an inbred line, a hybrid, a doubled haploid, or a plant of a segregating population.

The invention also relates to a method for the production of a plant having the modified PIN4 gene that leads to the capability of parthenocarpic fruit set by using a seed that comprises the modified PIN4 gene for growing the said plant.

The invention also relates to a method for seed production which may comprise growing plants from seeds of the invention, allowing the plants to produce seeds by allowing pollination to occur, and harvesting those seeds. Production of the seeds is suitably done by crossing or selfing. Preferably, the seeds so produced have the capability for parthenocarpic fruit set in the plants grown thereof.

In one embodiment, the invention relates to a method for the production of a plant having the modified PIN4 gene which leads to the capability of parthenocarpic fruit set, by using tissue culture of plant material that carries the modified PIN4 gene in its genome.

The invention furthermore relates to a method for the production of a plant having the modified PIN4 gene which leads to the capability of parthenocarpic fruit set, by using vegetative reproduction of plant material that carries the modified PIN4 gene in its genome.

The invention further provides a method for the production of a plant having the modified PIN4 gene by using a doubled haploid generation technique to generate a doubled haploid line from a plant which may comprise the modified PIN4 gene.

In one embodiment the invention relates to a method for the production of a plant that is capable of parthenocarpic fruit set, which may comprise modifying the CmPIN4 gene of SEQ ID No. 1, or modifying an orthologue of said PIN4 gene encoding a protein having any of the sequences as found in SEQ ID Nos 12-16, wherein the modification leads to an amino acid substitution in the encoded protein, and which modified protein leads to the induction of parthenocarpic fruit set. The modified protein suitably has a modification in the intracellular loop of the protein. Said modification can lead to a modified structure of the intracellular loop of the protein and/or a change in the functionality of the protein, which provides the plant with the capability of parthenocarpic fruit set.

The modification of the PIN4 gene can be introduced by means of mutagenesis. Mutagenesis may comprise the random introduction of at least one modification by means of one or more chemical compounds, such as ethyl methanesulphonate (EMS), nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol and ethylene oxide, and/or by physical means, such as UV-irradiation, fast-neutron exposure, X-rays, gamma irradiation, and/or by insertion of genetic elements, such as transposons, T-DNA, retroviral elements. Mutagenesis also may comprise the more specific, targeted introduction of at least one modification by means of homologous recombination, oligonucleotide-based mutation induction, zinc-finger nucleases (ZFNs), transcription activator-like effector nucleases (TALENs) or Clustered Regularly Interspaced Short Palindromic Repeat (CRISPR) systems.

In one embodiment the invention relates to a plant which may comprise the modified PIN4 gene as disclosed herein, whereby the modified PIN4 gene is obtained and/or identified by the use of TILLING.

In one embodiment the modified PIN4 gene is an exogenous PIN4 gene which can be introduced into a plant by a transgenic method or a cisgenic method. Use of a modified PIN4 gene of the invention for producing a plant that is capable of parthenocarpic fruit set may comprise the introduction of a modified exogenous PIN4 gene by a transgenic or a cisgenic method.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Induction of SNP Mutations in *Cucumis melo* by EMS

SNP mutations were induced in a population of *Cucumis melo* plants, with the goal to obtain parthenocarpic melon fruits. Approximately 10.000 seeds of a melon genotype were separated into two batches, which were treated with different EMS doses. For one batch a dose of 1.0% was used and for the other batch 1.5% EMS.

Seeds were germinated and 77 individuals were selected from which cuttings were made for further analysis. Phenotyping was done (Example 2) and DNA samples were obtained for further characterization and validation of the induced mutations.

Characterization of a number of the induced mutations showed that six of the induced SNP mutations were located in the PIN4 gene (Table 1). Based on these mutations, SNP markers were developed for further analysis.

Example 2

Phenotyping of *Cucumis melo* Plants with PIN4 Mutations

Cuttings of plants having mutations induced by EMS were observed in the greenhouse. The goal of this phenotyping trial was to determine the presence of parthenocarpic fruit set. Pollination of female flowers was therefore prevented.

In a first phenotyping trial in two of the mutant events, identified by plant numbers 320 and 431 (Table 1), each of which was represented by several cuttings having the identical mutation, parthenocarpic fruit set was observed. Parthenocarpic fruits showed a reasonable size, and had a very nice brix ranging from 9 to 15. Fruits ripened normally and had a taste comparable with the original parent. Non-pollinated fruits had no seeds. Furthermore, no empty cavity in the place of the usual seed cavity was observed (FIGS. 5A-B).

Further phenotyping of mutant plants also identified parthenocarpic fruit set in cuttings of the plant identified by number 363 (Table 1).

The female flowers of the identified plants appeared to develop normally. Male flowers of those plants were aborted or did not properly develop. After pollination with pollen from the original parent, fruits with seeds developed, showing that these mutant plants have facultative parthenocarpy.

Example 3

PIN4 Mutations in *Capsicum annuum*

A population of *Capsicum annuum* plants was also treated by EMS. DNA was sampled and was specifically analysed to identify mutations in the PIN4 gene of *Capsicum annuum*. A number of mutations were identified that resulted in an amino acid change in the intracellular loop of the CaPIN4 protein as presented in SEQ ID No. 13 (FIGS. 3A-B; Table 4). The presence of the modified protein in a *Capsicum annuum* plant results in parthenocarpy.

TABLE 4

PIN4 SNP mutations in *Capsicum annuum* and their effect on the encoded PIN4 protein

| Plant ID | Nt change | Mutation position on gDNA | Mutation position on CDS | Mutation Type | AAchange_pos |
|---|---|---|---|---|---|
| 508 | C-C/T | 1411 | 650 | AA change | A216V |
| 587 | C-T | 1767 | 1006 | AA change | P335S |
| 511 | G-G/A | 2190 | 1300 | AA change | G433S |
| 591 | G-G/A | 2325 | 1435 | AA change | G478R |

The invention is further described by the following numbered paragraphs:

1. Modified PIN4 gene, the wild type of which is as identified in SEQ ID No. 1, encoding the protein of SEQ ID No. 5, or the wild type of which encodes a protein that has a sequence similarity of at least 80% to SEQ ID No. 5, which modified PIN4 gene encodes a protein that comprises an amino acid change as a result of the modification, and which modified protein is capable of inducing parthenocarpic fruit set when present in a plant.

2. Modified PIN4 gene as claimed in claim 1, the wild type of which encodes a protein as identified in SEQ ID No. 5, or SEQ ID No. 12, or SEQ ID No. 13, or SEQ ID No. 14, or SEQ ID No. 15, or SEQ ID No. 16, which modified gene encodes a modified protein that comprises an amino acid change in the intracellular loop of the protein structure as a result of the modification, which altered protein is capable of inducing parthenocarpic fruit set when present in a plant.

3. Modified PIN4 gene as claimed in claim 1 or 2, wherein the amino acid change of the protein results in a change in the structure of the protein, which change in structure leads to the capability of parthenocarpic fruit set when the protein is present in a plant.

4. Modified PIN4 gene as claimed in any of the claims 1-3, wherein the modification results in a non-conservative amino acid substitution.

5. Modified PIN4 gene as claimed in any of the claims 1-4, wherein the modification results in substitution of a negatively charged or uncharged amino acid with a positively charged amino acid, of a polar amino acid with a hydrophobic amino acid, of an uncharged polar amino acid with a hydrophobic amino acid, of a hydrophobic amino acid with a non-hydrophobic amino acid, of a negatively charged amino acid with a positively charged or uncharged amino acid or in substitution with an amino acid resulting in a different structural conformation.

6. Modified PIN4 gene as claimed in any of the claims 1-5, wherein the modification results in the substitution of glutamic acid with lysine, or in the substitution of aspartic acid with histidine.

7. Modified PIN4 gene as claimed in claim 6, wherein the modified gene encodes a protein having a glutamic acid substitution on position 414 of SEQ ID No. 5, preferably a glutamic acid to lysine substitution resulting in SEQ ID No. 7, or the encoded protein comprises a glutamic acid substitution, preferably a glutamic acid to lysine substitution, on position 414 of SEQ ID No. 12, or on position 420 of SEQ ID No. 13, or the encoded protein comprises an aspartic acid substitution, preferably an aspartic acid to histidine substitution, on position 416 of SEQ ID No. 14, or on position 416 of SEQ ID No. 15, or on position 419 of SEQ ID No. 16.

8. Modified PIN4 gene as claimed in any one of the claims 1-5, wherein the modification results in a non-conservative amino acid substitution of proline, preferably a substitution of proline with leucine.

9. Modified PIN4 gene as claimed in claim 8, wherein the modified gene encodes a protein having a non-conservative proline substitution on position 166 of SEQ ID No. 5, or of SEQ ID No. 12, or of SEQ ID No. 13, or of SEQ ID No. 14, or of SEQ ID No. 15, or of SEQ ID No. 16, which substitution is preferably a proline to leucine substitution.

10. Modified PIN4 gene as claimed in any one of the claims 1-5, wherein the modification results in a non-conservative amino acid substitution of serine or cysteine, preferably in the substitution of serine or cysteine with tyrosine.

11. Modified PIN4 gene as claimed in claim 10, wherein the modified gene encodes a protein having a non-conservative serine substitution on position 295 of SEQ ID No. 5, or of SEQ ID No. 12, or of SEQ ID No. 14, which substitution is preferably a serine to tyrosine substitution, or the modified gene encodes a protein having a non-conservative cysteine substitution on position 290 of SEQ ID No. 13, or of SEQ ID No. 15, or of SEQ ID No. 16, which substitution is preferably a cysteine to tyrosine substitution.

12. Plant comprising a modified PIN4 gene as claimed in any of the claims 1-11, which plant is capable of parthenocarpic fruit set as a result of the presence of the modified protein encoded by the modified PIN4 gene.

13. Seed comprising a modified PIN4 gene as claimed in any of the claims 1-11, wherein the plant grown from the seed is capable of parthenocarpic fruit set as a result of the presence of the modified protein.

14. Plant as claimed in claim 12, or seed as claimed in claim 13, which is a plant or a seed of any of the species *Cucumis melo, Cucumis sativus, Citrullus lanatus, Solanum lycopersicum, Solanum melongena*, or *Capsicum annuum*, preferably of the species *Cucumis melo*.

15. *Cucumis melo* plant comprising a modified PIN4 gene encoding a modified PIN4 protein, which modification results in the capability of parthenocarpic fruit set.

16. *Cucumis melo* plant as claimed in claim 15, wherein the modified protein is represented by SEQ ID No. 6, or by SEQ ID No. 7, or by SEQ ID No. 18.

17. Progeny of a plant as claimed in claim 12 or 14-16, or of a seed as claimed in claim 13 or 14, comprising a modified PIN4 gene as claimed in any of the claims 1-11, which progeny plant is capable of parthenocarpic fruit set as a result of the presence of the modified protein.

18. Method for the production of a seedless fruit, in particular a seedless *Cucumis melo* fruit, comprising providing a plant having a modified PIN4 gene as claimed in any of the claims 1-11, growing said plant, and allowing the fruit to develop without pollination.

19. Seedless fruit produced by the method as claimed in claim 18.

20. Fruit comprising a modified PIN4 gene as claimed in any of the claims 1-11.

21. Fruit as claimed in claim 20, wherein the fruit is seedless.

22. Fruit as claimed in claim 20, wherein the fruit has seed as a result of pollination of the stigma of a plant comprising a modified PIN4 gene as claimed in any of the claims 1-11.

23. Use of a modified PIN4 gene as claimed in any of the claims 1-11 for producing a plant that is capable of parthenocarpic fruit set, preferably a plant of the species *Cucumis melo, Cucumis sativus, Citrullus lanatus, Solanum lycopersicum, Solanum melongena*, or *Capsicum annuum*, more preferably a *Cucumis melo* plant.

24. Use as claimed in claim 23, wherein the plant that is capable of parthenocarpic fruit set is produced by introduction of the modified PIN4 gene into its genome, in particular by means of introgression.

25. Use of a plant as claimed in claim 12 or claim 14-16, or of progeny as claimed in claim 17, for the production of a seedless fruit, in particular for the production of a seedless *Cucumis melo* fruit.

26. Use of a molecular marker to identify a modification in a PIN4 gene which leads to the capability of parthenocarpic fruit set in a plant, preferably a marker to identify a SNP at position 497 or position 1240 or position 884 of SEQ ID No. 2, or to identify a SNP resulting in an amino acid substitution at position 166 or position 414 or position 295 of SEQ ID No. 5, or to identify a SNP resulting in an amino acid substitution at the corresponding positions of SEQ ID Nos. 12-16.

27. Use of a molecular marker as claimed in claim 26, wherein the SNP at position 497 is from C to T, the SNP at position 1240 is from G to A, and the SNP at position 884 is from C to A.

28. Molecular marker comprising a SNP at position 497 or position 1240 or position 884 of SEQ ID No. 2, in particular a SNP at position 497 from C to T, a SNP at position 1240 from G to A, or a SNP at position 884 from C to A.

29. Method for producing a plant that is capable of parthenocarpic fruit set, comprising modifying the CmPIN4 gene of SEQ ID No. 1, or modifying an orthologue of said PIN4 gene encoding a protein having any of the sequences as found in SEQ ID Nos. 12-16, wherein the modification leads to an amino acid substitution in the encoded protein, and the presence of such modified protein leads to the capability of parthenocarpic fruit set.

30. Method as claimed in claim 29, wherein the PIN4 gene is an endogenous gene.

Having thus described in detail preferred embodiments of the present invention, it is to be understood that the invention is not to be limited to particular details set forth in the above description as many apparent variations thereof are possible without departing from the spirit or scope of the present invention.

The invention claimed is:

1. A hand of man modified PIN4 gene, the wild type of which is as identified in SEQ ID NO: 1, encoding the protein of SEQ ID NO: 5, or the wild type of which encodes a protein that has a sequence identity of at least 90% to SEQ ID NO: 5, which modified PIN4 gene encodes a protein that comprises a non-conservative amino acid change in amino acids 411-414 of SEQ ID NO: 5 or in a corresponding position of a protein that has a sequence identity of at least 90% to SEQ ID NO: 5, which results in a change in the structure of the protein, which change in structure leads to the capability of parthenocarpic fruit set when the protein is present in a plant.

2. The modified PIN4 gene as claimed in claim 1, the wild type of which encodes a protein as identified in SEQ ID NO: 5, SEQ ID NO: 12, or SEQ ID NO 14.

3. The modified PIN4 gene as claimed in claim 1, wherein the modification results in substitution of a negatively charged or uncharged amino acid with a positively charged amino acid, of a polar amino acid with a hydrophobic amino acid, of an uncharged polar amino acid with a hydrophobic amino acid, of a hydrophobic amino acid with a non-hydrophobic amino acid, of a negatively charged amino acid with a positively charged or uncharged amino acid or in substitution with an amino acid resulting in a different structural conformation.

4. The modified PIN4 gene as claimed in claim 1, wherein the modification results in the substitution of glutamic acid with lysine, or in the substitution of aspartic acid with histidine.

5. The modified PIN4 gene as claimed in claim 4, wherein the modified gene encodes a protein having a glutamic acid substitution at position 414 of SEQ ID NO: 5, or position 414 of SEQ ID NO: 12.

6. A plant comprising the modified PIN4 gene as claimed in claim 1, which plant is capable of parthenocarpic fruit set as a result of the presence of the modified protein encoded by the modified PIN4 gene.

7. A seed comprising the modified PIN4 gene as claimed in claim 1, wherein the plant grown from the seed is capable of parthenocarpic fruit set as a result of the presence of the modified protein.

8. The plant as claimed in claim 6, or the seed as claimed in claim 7, which is a plant or a seed of any of the species *Cucumis melo, Cucumis sativus, Citrullus lanatus, Solanum lycopersicum, Solanum melongena*, or *Capsicum annuum*, preferably of the species *Cucumis melo*.

9. The modified PIN4 gene as claimed in claim 5, wherein the glutamic acid substitution is a glutamic acid to lysine substitution.

10. The modified PIN4 gene as claimed in claim 4, wherein the modified gene encodes a protein with an aspartic acid substitution at position 416 of SEQ ID NO: 14.

11. The modified PIN4 gene as claimed in claim 10, wherein the aspartic acid substitution is an aspartic acid to histidine substitution.

* * * * *

UNITED STATES PATENT AND TRADEMARK OFFICE
CERTIFICATE OF CORRECTION

PATENT NO. : 10,941,411 B2
APPLICATION NO. : 15/656109
DATED : March 9, 2021
INVENTOR(S) : Cornelis Maria Petrus Van Dun et al.

It is certified that error appears in the above-identified patent and that said Letters Patent is hereby corrected as shown below:

In the Claims

Claim 2, should read:
2. The modified PIN4 gene as claimed in claim 1, the wild type of which encodes a protein as identified in SEQ ID NO: 5, SEQ ID NO: 12, or SEQ ID NO: 14.

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*